(12) United States Patent
Barta et al.

(10) Patent No.: US 10,980,801 B2
(45) Date of Patent: *Apr. 20, 2021

(54) PHENYLPIPERAZINE PROPROTEIN CONVERTASE SUBTILISIN/KEXIN TYPE 9 (PCSK9) MODULATORS AND THEIR USE

(71) Applicant: SRX Cardio, LLC, Pittsford, NY (US)

(72) Inventors: Thomas E. Barta, Carrboro, NC (US); Jonathan William Bourne, Fairport, NY (US); Kyle D. Monroe, Pittsford, NY (US); Michael M. Muehlemann, Liverpool, NY (US); Anjali Pandey, Fremont, CA (US); Simeon Bowers, Oakland, CA (US)

(73) Assignee: SRX Cardio, LLC, Pittsford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/739,544

(22) Filed: Jan. 10, 2020

(65) Prior Publication Data

US 2020/0253958 A1    Aug. 13, 2020

Related U.S. Application Data

(63) Continuation of application No. 15/753,790, filed as application No. PCT/US2016/047816 on Aug. 19, 2016, now Pat. No. 10,568,882.

(60) Provisional application No. 62/208,072, filed on Aug. 21, 2015, provisional application No. 62/298,890, filed on Feb. 23, 2016.

(51) Int. Cl.
| | | |
|---|---|---|
| A61K 31/495 | (2006.01) | |
| A61P 3/06 | (2006.01) | |
| A61K 31/4409 | (2006.01) | |
| A61K 45/06 | (2006.01) | |
| C07D 213/64 | (2006.01) | |
| C07C 237/20 | (2006.01) | |

(52) U.S. Cl.
CPC ........ *A61K 31/495* (2013.01); *A61K 31/4409* (2013.01); *A61K 45/06* (2013.01); *A61P 3/06* (2018.01); *C07C 237/20* (2013.01); *C07D 213/64* (2013.01); *A61K 2300/00* (2013.01); *C07B 2200/07* (2013.01)

(58) Field of Classification Search
None
See application file for complete search history.

(56) References Cited

U.S. PATENT DOCUMENTS

| 4,064,245 | A | 12/1977 | Beregi et al. | |
|---|---|---|---|---|
| 7,750,012 | B2 | 7/2010 | Sandanayaka et al. | |
| 8,673,850 | B2 | 3/2014 | Seidah et al. | |
| 10,568,882 | B2 * | 2/2020 | Barta | A61P 3/06 |
| 2004/0254120 | A1 | 12/2004 | Fogelman et al. | |
| 2009/0203676 | A1 | 8/2009 | Barba et al. | |
| 2010/0113782 | A1 | 5/2010 | Bolin et al. | |
| 2013/0064825 | A1 | 3/2013 | Chan et al. | |
| 2014/0045854 | A1 | 2/2014 | Uesugi et al. | |
| 2014/0093513 | A1 | 4/2014 | Milne et al. | |
| 2015/0051144 | A1 | 2/2015 | Pingali et al. | |
| 2015/0111857 | A1 | 4/2015 | Hodous et al. | |

FOREIGN PATENT DOCUMENTS

| EP | 0378207 | 7/1990 |
|---|---|---|
| WO | WO-95/00161 | 1/1995 |
| WO | WO 2004/069792 | 8/2004 |
| WO | WO 2006/049597 | 5/2006 |
| WO | WO 2006/125665 | 11/2006 |
| WO | WO 2007/009741 | 1/2007 |
| WO | WO 2014/127316 | 8/2014 |
| WO | WO 2014/150395 | 9/2014 |
| WO | WO 2014/150983 | 9/2014 |
| WO | WO 2016/107602 | 7/2016 |
| WO | WO 2016/107603 | 7/2016 |
| WO | WO-2018/026866 | 2/2018 |

OTHER PUBLICATIONS

STN Registry Database for CAS Registry 758671-90-3, entry date of Oct. 8, 2004, Accessed Sep. 26, 2019, 1 page.
STN Registry Database for CAS RN 769101-76-0, entry date of Oct. 26, 2004, Accessed Feb. 18, 2020, 1 page.
Annoura et al., "A novel class of Na+ and Ca2+ channel dual blockers with highly potent anti-ischemic effects", Bioorganic and Medicinal Chemistry Letters 9, (1999), pp. 2999-3002.
Extended European Search Report for EP Appln. No. 16839893.1 dated Feb. 15, 2019, 10 pages.
International Search Report and Written Opinion for PCT/US2016/047816 dated Nov. 16, 2016, 8 pages.
Pubchem CID 28917034 Create Date: May 28, 2009 p. 3, Fig. Retrieved from the Internet: <URL: https://pubchem.ncbi.nlm.nih.gov/compound/28917034>.

* cited by examiner

*Primary Examiner* — Zinna Northington Davis
(74) *Attorney, Agent, or Firm* — Sheppard Mullin Richter & Hampton LLP

(57) ABSTRACT

This invention is related to the field of PCSK9 biology and the composition and methods of use of small organic compounds as ligands for modulation of PCSK9 biological activity. In particular, the invention provides compositions of small organic compounds that modulate circulating levels of low density lipoproteins by altering the conformation of the protein PCSK9. Binding these small organic compound ligands to PCSK9 alters the conformation of the protein, modifying the interaction between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for small organic compound ligands that can raise LDL levels.

15 Claims, 2 Drawing Sheets

PHENYLPIPERAZINE PROPROTEIN CONVERTASE SUBTILISIN/KEXIN TYPE 9 (PCSK9) MODULATORS AND THEIR USE

This application is a continuation of U.S. application Ser. No. 15/753,790, filed Feb. 20, 2018, which is a U.S. National Stage Application under 35 U.S.C. § 371 of International Application No. PCT/US2016/047816, filed Aug. 19, 2016, which claims priority benefit of U.S. Application No. 62/208,072, filed Aug. 21, 2015 and U.S. Application No. 62/298,890 filed Feb. 23, 2016, the contents of each of which are hereby incorporated by reference in their entirety into the present disclosure.

FIELD OF INVENTION

This invention is related to the field of PCSK9 biology. In particular, the invention provides compositions and methods of use of small organic compounds as ligands that directly bind with the PCSK9 protein, and differentially modify PCSK9 biological activity in cells. These changes may include alteration in PCSK9 binding to, or dissociating from, LDLR, changes in LDLR number on the cell surface, or changes in the rate of LDL internalization.

BACKGROUND

Elevated plasma levels of low density lipoprotein cholesterol (LDL-C) represent the greatest risk factor for the development of coronary heart disease. Clearance of LDL-C from the plasma occurs primarily by the liver through the action of LDL receptors (LDLRs), which are cell surface glycoproteins that bind to apolipoprotein B100 (apoB100) on LDL particles with high affinity and mediate their endocytic uptake. Goldstein et al., *Annu. Rev. Cell Biol.* 1:1-39 (1985). Autosomal dominant hypercholesterolemia (ADH) is associated with mutations that reduce plasma LDL clearance that are found in genes encoding the LDLR (familial hypercholesterolemia (FH)) or apoB100 (familial defective apoB100). Hobbs et al., *Annu. Rev. Genet.* 24, 133-170 (1990); and Innerarity et al., *J. Lipid Res.* 31:1337-1349 (1990), respectively.

The low density lipoprotein (LDL) receptor (LDLR) mediates efficient endocytosis of VLDL, VLDL remnants, and LDL. As part of the endocytic process, the LDLR releases lipoproteins into hepatic endosomes.

One approach to modulating LDL-cholesterol levels would be to identify small organic compounds that bind to PCSK9 and alter the kinetics of the interaction between PCSK9 and the LDLR such that the rate of lipoprotein clearance by LDLR endocytosis is increased or decreased, as desired.

SUMMARY OF THE INVENTION

This invention is related to the field of PCSK9 biology and treatment of hypercholesterolemia and hypocholesterolemia. In particular, the invention provides compositions of ligands that bind and alter PCSK9 biological conformation and methods that use these ligands to modify PCSK9 activity to change circulating levels of low density lipoprotein in the blood. These ligands may be small organic compounds, and more preferably small organic compounds less than 600 Da. Altering the conformation of PCSK9 can change the interactions between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for ligands that can raise LDL levels.

Phenylpiperazine Scaffold:

In one embodiment, the present invention contemplates a phenylpiperazine small organic compound comprising of a phenylpiperazine scaffold of Formula I:

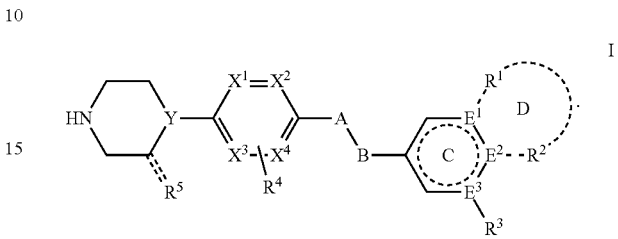

wherein i) A is selected from the group consisting of —O—, —CO—, —CH$_2$—, —CF$_2$—, —SO$_2$—; ii) if A is —CH$_2$ or —CF$_2$ then B is absent, and if A is —O— then B is absent or —CH$_2$, and, if A is —CO or SO$_2$ then B is —NH—; iii) Ring C is a 5 or 6 membered saturated or unsaturated aryl, heteroaryl, carbocyclic or heterocyclic ring, wherein ring C may be optionally fused with $R^1$, $R^2$ to form a 5-6 membered aryl, heteroaryl, carbocyclic or heterocyclic ring; iv) $E^1$, $E^2$, and $E^3$ are independently selected from C, CH, or N; v) if B is absent or —CH$_2$— then $R^1$ and $R^2$ are independently selected from the group consisting of H, lower alkyl, hydroxy, amino, aminoalkyl, hydroxyalkyl, haloalkyl, carboxy, —CONH$_2$, nitrile, —S-alkyl, —O-alkyl, acyl, and oxo; vi) if B is —NH— then $R^1$, $R^2$, and $R^3$ are independently selected from the group consisting of H, lower alkyl, hydroxy, amino, aminoalkyl, hydroxyalkyl, haloalkyl, carboxy, —CONH$_2$, —CON-alkyl, nitrile, —S-alkyl, —O-alkyl, acyl, oxo; or $R^1$ and $R^2$ with the atoms attached thereof combine to form a 5-6 membered fused saturated or unsaturated ring D containing 0-3 heteroatoms where Ring D may further be substituted at positions at least two atoms away from the juncture with Ring C; vi) $R^4$ is selected from the group consisting of H, OH, halogen, and lower alkyl; vii) $R^5$ is selected from the group consisting of H$_2$, and O; vii) Y is selected form the group consisting of N, and CH; and viii) $X^{1-4}$ are independently selected from the group consisting of CH, C—$R^4$, or N. Also provided are pharmaceutically acceptable salts, hydrates, solvates, tautomeric forms, and stereoisomers of these compounds. In one embodiment the compound is selected from the group comprising of:

N-phenyl-4-(piperazin-1-yl)benzenesulfonamide;
N-isopropyl-4-((4-(piperazin-1-yl)phenyl)sulfonamido) benzamide;
N-methyl-4-((4-(piperazin-1-yl)phenyl)sulfonamido)benzamide;
N-cyclopentyl-4-(piperazin-1-yl)benzenesulfonamide;
N-cyclohexyl-4-(piperazin-1-yl)benzenesulfonamide;
N-(3,4-dimethylphenyl)-4-(piperazin-1-yl)benzenesulfonamide;
N-(3,5-dimethylphenyl)-4-(piperazin-1-yl)benzenesulfonamide;
N-(3,5-dichlorophenyl)-4-(piperazin-1-yl)benzenesulfonamide;
4-(piperazin-1-yl)-N-(5,6,7,8-tetrahydronaphthalen-2-yl) benzenesulfonamide;
N-(naphthalen-2-yl)-4-(piperazin-1-yl)benzenesulfonamide;

N-(cinnolin-7-yl)-4-(piperazin-1-yl)benzenesulfonamide;
N-(isoquinolin-7-yl)-4-(piperazin-1-yl)benzenesulfonamide;
4-(piperazin-1-yl)-N-(quinolin-6-yl)benzenesulfonamide;
N-(cinnolin-6-yl)-4-(piperazin-1-yl)benzenesulfonamide;
4-(piperazin-1-yl)-N-(quinoxalin-6-yl)benzenesulfonamide;
4-(piperazin-1-yl)-N-(pyrido[2,3-b]pyrazin-7-yl)benzenesulfonamide;
N-(1H-benzo[d][1,2,3]triazol-5-yl)-4-(piperazin-1-yl)benzenesulfonamide;
N-(2-methylbenzo[b]thiophen-5-yl)-4-(piperazin-1-yl)benzenesulfonamide;
N-(2-oxo-1,2,3,4-tetrahydroquinolin-7-yl)-4-(piperazin-1-yl)benzenesulfonamide;
N-(benzo[c][1,2,5]thiadiazol-5-yl)-4-(piperazin-1-yl)benzenesulfonamide;
N-(1H-indol-6-yl)-4-(piperazin-1-yl)benzenesulfonamide;
N-(1H-indol-5-yl)-4-(piperazin-1-yl)benzenesulfonamide;
N-(benzo[d]isoxazol-5-yl)-4-(piperazin-1-yl)benzenesulfonamide;
N-(2-aminoimidazo[1,2-a]pyrimidin-6-yl)-4-(piperazin-1-yl)benzenesulfonamide;
N-(2,3-dihydrobenzofuran-6-yl)-4-(piperazin-1-yl)benzenesulfonamide;
N-(2,3-dihydrobenzofuran-5-yl)-4-(piperazin-1-yl)benzenesulfonamide;
N-(2,2-difluorobenzo[d][1,3]dioxol-5-yl)-4-(piperazin-1-yl)benzenesulfonamide;
N-phenyl-4-(piperazin-1-yl)benzamide;
N-(cinnolin-7-yl)-4-(piperazin-1-yl)benzamide;
4-(piperazin-1-yl)-N-(5,6,7,8-tetrahydronaphthalen-2-yl)benzamide;
1-(4-(phenylsulfonyl)phenyl)piperazine;
1-(4-((4-chlorophenyl)sulfonyl)phenyl)piperazine;
4-((4-(piperazin-1-yl)phenyl)sulfonyl)phenol;
1-methyl-4-((4-(piperazin-1-yl)phenyl)sulfonyl)pyridin-2(1H)-one;
4-((4-(piperazin-1-yl)phenyl)sulfonyl)pyridin-2(1H)-one;
1-(4-(difluoro(phenyl)methyl)phenyl)piperazine;
1-(4-(difluoro(pyridin-3-yl)methyl)phenyl)piperazine;
3-(difluoro(4-(piperazin-1-yl)phenyl)methyl)phenol;
phenyl(4-(piperazin-1-yl)phenyl)methanone;
1-(4-benzylphenyl)piperazine;
1-(4-(benzyloxy)phenyl)piperazine;
1-(4-phenoxyphenyl)piperazine;
1-(4-(4-bromophenoxy)phenyl)piperazine;
1-(4-(4-(methylthio)phenoxy)phenyl)piperazine;
4-(4-(piperazin-1-yl)phenoxy)benzoic acid;
4-(4-(piperazin-1-yl)phenoxy)benzamide;
2-bromo-4-(4-(piperazin-1-yl)phenoxy)benzoic acid;
5-(4-(piperazin-1-yl)phenoxy)picolinamide;
1-(4-(3,4-difluorophenoxy)phenyl)piperazine;
1-(4-(3,4-dimethylphenoxy)phenyl)piperazine;
2-hydroxy-N-phenyl-4-(piperazin-1-yl)benzenesulfonamide;
4-(2-oxopiperazin-1-yl)-N-phenylbenzenesulfonamide;
2-fluoro-4-(2-oxopiperazin-1-yl)-N-phenylbenzenesulfonamide;
2-hydroxy-N-phenyl-4-(piperazin-1-yl)benzamide;
1-(4-(difluoro(phenyl)methyl)-3-fluorophenyl)piperazin-2-one;
2-(phenylsulfonyl)-5-(piperazin-1-yl)phenol;
N-phenyl-4-(piperazin-1-yl-2,2,6,6-$d_4$)benzenesulfonamide;
4-(4-phenoxyphenyl)piperidine;
4-(4-(cyclohexyloxy)phenyl)piperidine;
4-(4-((tetrahydro-2H-pyran-4-yl)oxy)phenyl)piperidine;
4-(4-(piperidin-4-yl)phenoxy)piperidine;
1-(4-(cyclohexyloxy)phenyl)piperazine;
1-(4-((tetrahydro-2H-pyran-4-yl)oxy)phenyl)piperazine;
1-(4-(piperidin-4-yl)oxy)phenyl)piperazine;
N-phenyl-4-(piperidin-4-yl)benzenesulfonamide;
4-(piperidin-4-yl)-N-(5,6,7,8-tetrahydronaphthalen-2-yl)benzenesulfonamide;
N-phenyl-4-(piperidin-4-yl)benzamide;
4-(4-(difluoro(phenyl)methyl)phenyl)piperidine;
phenyl(4-(piperidin-4-yl)phenyl)methanone;
2-ethyl-N-phenyl-4-(piperazin-1-yl)benzamide;
1-(4-phenoxyphenyl)piperazin-2-one;
1-(4-(4-fluorobenzyl)phenyl)piperazine;
6-(4-(piperazin-1-yl)phenoxy)pyrimidin-4(3H)-one;
4-((4-(piperazin-1-yl)phenyl)sulfonyl)morpholine;
1-(4-(pyrrolidin-1-ylsulfonyl)phenyl)piperazine;
1-(2-fluoro-4-(phenylsulfonyl)phenyl)piperazine;
4-(piperazin-1-yl)benzenesulfonamide;
N-methyl-4-(piperazin-1-yl)benzenesulfonamide;
N-cyclopropyl-4-(piperazin-1-yl)benzenesulfonamide;
N-isopropyl-4-(piperazin-1-yl)benzenesulfonamide;
N-((4-(piperazin-1-yl)phenyl)sulfonyl)acetamide;
N-(4-(piperazin-1-yl)phenyl)methanesulfonamide;
N-(4-(piperazin-1-yl)phenyl)ethanesulfonamide;
N-(4-(piperazin-1-yl)phenyl)benzenesulfonamide;
4-(piperazin-1-yl)-N-(pyridin-4-yl)benzenesulfonamide;
N-(4-(piperazin-1-yl)phenyl)ethanesulfonamide;
N-(4-(piperazin-1-yl)phenyl)benzenesulfonamide;
4-(piperazin-1-yl)-N-(pyridin-3-yl)benzenesulfonamide;
4-(piperazin-1-yl)-N-(pyridin-2-yl)benzenesulfonamide;
4-(piperazin-1-yl)-N-(thiazol-2-yl)benzenesulfonamide;
4-(piperazin-1-yl)-N-(quinolin-7-yl)benzenesulfonamide;
N-phenyl-6-(piperazin-1-yl)pyridine-3-sulfonamide;
N-phenyl-5-(piperazin-1-yl)pyridine-2-sulfonamide;
N-(3,5-difluorophenyl)-4-(piperazin-1-yl)benzenesulfonamide;
N-(2,3-dihydro-1H-inden-2-yl)-4-(piperazin-1-yl)benzenesulfonamide;
3-fluoro-4-(piperazin-1-yl)-N-(5,6,7,8-tetrahydronaphthalen-2-yl)benzenesulfonamide;
6-(piperazin-1-yl)-N-(5,6,7,8-tetrahydronaphthalen-2-yl)pyridine-3-sulfonamide;
5-(piperazin-1-yl)-N-(5,6,7,8-tetrahydronaphthalen-2-yl)pyridine-2-sulfonamide;
N-phenyl-4-(piperidin-4-yl)benzenesulfonamide;
4-(piperidin-4-yl)-N-(5,6,7,8-tetrahydronaphthalen-2-yl)benzenesulfonamide;
1-(4-phenoxyphenyl)piperazine-2,2,3,3,5,5,6,6-$d_8$;
and 1-(4-(4-fluorobenzyl)phenyl)piperazine-2,2,3,3,5,5,6,6-$d_8$;
or a pharmaceutical composition thereof.

In one embodiment, compounds of Formula I where one or more atoms are substituted with an isotope are also contemplated. For example. 1-(4-phenoxyphenyl)piperazine is selectively substituted with deuterium to form the compound 1-(4-phenoxyphenyl)piperazine-2,2,3,3,5,5,6,6-$d_8$. Another example, 1-(4-(4-fluorobenzyl)phenyl)piperazine is selectively substituted with deuterium to form the compound 1-(4-(4-fluorobenzyl)phenyl)piperazine-2,2,3,3,5,5,6,6-$d_8$.
Other examples of isotopes that can be incorporated into compounds of the disclosure include isotopes of hydrogen, carbon, nitrogen, oxygen, phosphorous, fluorine and chlorine, such as, but not limited to $^2$H (deuterium, d), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I.

In one embodiment, the present invention contemplates a phenylpiperazine small organic compound comprising of a phenylpiperazine scaffold of Formula II:

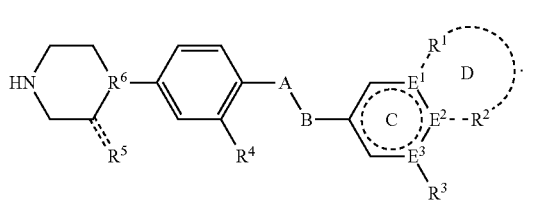

wherein i) A is selected from the group consisting of —O—, —CO—, —CH$_2$—, —CF$_2$—, —SO$_2$—; ii) if A is —CH$_2$ or —CF$_2$ then B is nothing, if A is —O— then B is nothing or —CH$_2$, if A is —CO or SO$_2$ then B is —NH—; iii) Ring C is a 5 or 6 membered saturated or unsaturated aryl, heteroaryl, carbocyclic or heterocyclic ring. And ring C may be fused via R$^1$, R$^2$ to form a 5-6 membered aryl, heteroaryl, carbocyclic or heterocyclic ring; iv) E$^1$, E$^2$, and E$^3$ are independently selected from C or N; v) if B is nothing or —CH$_2$— then R$^1$ and R$^2$ are independently selected from the group consisting of lower alkyl, hydroxy, amino, aminoalkyl, hydroxylalky, haloalkyl, carboxy, —CONH$_2$, nitrile, —S-alkyl, —O-alkyl, acyl, and oxo; vi) if B is —NH— then R$^1$, R$^2$, and R$^3$ are independently selected from the group consisting of lower alkyl, hydroxy, amino, aminoalkyl, hydroxylalky, haloalkyl, carboxy, —CONH$_2$, —CON-alkyl, nitrile, —S-alkyl, —O-alkyl, acyl, oxo; and R$^1$ and R$^2$ may be joined to form a 5-6 membered fused saturated or unsaturated ring D containing 0-3 heteroatoms where Ring D may further be substituted at positions at least two atoms away from the juncture with Ring C; vi) R$^4$ is selected from the group consisting of H, OH, halogen, and lower alkyl; vii) R$^5$ is selected from the group consisting of H$_2$, and O; vii) R$^6$ is selected form the group consisting of N, and CH.

In one embodiment, the present invention contemplates a phenylpiperazine small organic compound comprising of a phenylpiperazine scaffold of Formula III:

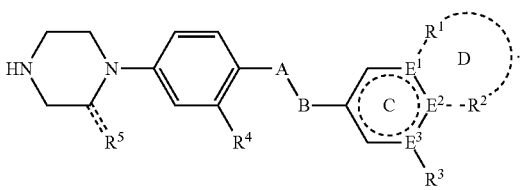

wherein i) A is selected from the group consisting of —O—, —CO—, —CH$_2$—, —CF$_2$—, —SO$_2$—; ii) if A is —CH$_2$ or —CF$_2$ then B is nothing, if A is —O— then B is nothing or —CH$_2$, if A is —CO or SO$_2$ then B is —NH—; iii) Ring C is a 5 or 6 membered aryl, heteroaryl, carbocyclic or heterocyclic ring. And ring C may be fused via R$^1$, R$^2$ to form a 5-6 membered aryl, heteroaryl, carbocyclic or heterocyclic ring; iv) E$^1$, E$^2$, and E$^3$ are independently selected from C or N; v) if B is nothing or —CH$_2$— then R$^1$ and R$^2$ are independently selected from the group consisting of lower alkyl, hydroxy, amino, aminoalkyl, hydroxylalky, haloalkyl, carboxy, —CONH$_2$, nitrile, —S-alkyl, —O-alkyl, acyl, and oxo; vi) if B is —NH— then R$^1$, R$^2$, and R$^3$ are independently selected from the group consisting of lower alkyl, hydroxy, amino, aminoalkyl, hydroxylalky, haloalkyl, carboxy, —CONH$_2$, —CON-alkyl, nitrile, —S-alkyl, —O-alkyl, acyl, oxo; and R$^1$ and R$^2$ may be joined to form a 5-6 membered fused ring D containing 0-3 heteroatoms where Ring D may further be substituted at positions at least two atoms away from the juncture with Ring C; vi) R$^4$ is selected from the group consisting of H, OH, and halogen; vii) R$^5$ is selected from the group consisting of H$_2$, and O.

Compound Methods of Use:

In one embodiment, the present invention contemplates a method, comprising: a) providing; i) a PCSK9 protein, wherein said protein comprises a binding site that induces allosteric modulation and a low density lipoprotein receptor binding site; ii) a small organic compound capable of binding to said binding site, and selected from the group consisting of a compound of a phenylpiperazine scaffold of Formula I; iii) a plurality of hepatocyte cells comprising a low density lipoprotein receptor and low density lipoproteins; b) binding said small organic compound to said binding site, wherein said small organic compound induces a conformational shift of said protein; and c) modulating the rate of low density lipoprotein receptor internalization by said plurality of hepatocytes by said conformational shift. In one embodiment the present invention contemplates a method, wherein said small organic compound induces a conformational change of the PCSK9 protein, such that the rate of low density lipoprotein receptor internalization by a plurality of hepatocytes is increased.

In one embodiment, the present invention contemplates a method, comprising: a) providing; i) a PCSK9 protein, wherein said protein comprises a binding site that induces allosteric modulation and a low density lipoprotein receptor binding site; ii) a small organic compound capable of binding to said binding site, and selected from the group consisting of a compound of a phenylpiperazine scaffold of Formula I; iii) a plurality of hepatocyte cells comprising a low density lipoprotein receptor and low density lipoproteins; b) binding said small organic compound to said binding site, wherein said small organic compound induces a conformational shift of said protein; and c) modulating the affinity of said low density lipoprotein receptor binding site for said low density lipoprotein receptor by said conformational shift.

In one embodiment, the small organic compound is an allosteric inhibitor ligand wherein said modulating decreases the affinity of said low density lipoprotein receptor binding site for said low density lipoprotein receptor such that internalization of said low density lipoprotein by said plurality of hepatocytes is increased. In one embodiment, the conformational shift of said protein is selected from the group consisting of an induced fit shift and a biomechanical shift. In one embodiment the small organic compound is a small molecule compound. In one embodiment, the small organic compound is selected from the group consisting of a phenylpiperazine scaffold of Formula I. In one embodiment, the small organic compound is selected from the group consisting of a phenylpiperazine scaffold of Formula I, wherein one or more atoms are substituted with an isotope are also contemplated. Also provided are pharmaceutically acceptable salts, hydrates, solvates, tautomeric forms, and stereoisomers of these compounds selected from the group consisting of a phenylpiperazine scaffold of Formula I.

In one embodiment, the small organic compound is an allosteric inhibitor ligand wherein said modulating decreases the affinity of said low density lipoprotein receptor binding site for said low density lipoprotein receptor such that internalization of said low density lipoprotein by said plurality of hepatocytes is increased. In one embodiment, the conformational shift of said protein is selected from the group consisting of an induced fit shift and a biomechanical shift. In one embodiment, the small organic compound is a small molecule compound. In one embodiment, the small organic compound is selected from the group comprising of:

N-phenyl-4-(piperazin-1-yl)benzenesulfonamide;
N-isopropyl-4-((4-(piperazin-1-yl)phenyl)sulfonamido)benzamide;
N-methyl-4-((4-(piperazin-1-yl)phenyl)sulfonamido)benzamide;
N-cyclopentyl-4-(piperazin-1-yl)benzenesulfonamide;
N-cyclohexyl-4-(piperazin-1-yl)benzenesulfonamide;
N-(3,4-dimethylphenyl)-4-(piperazin-1-yl)benzenesulfonamide;
N-(3,5-dimethylphenyl)-4-(piperazin-1-yl)benzenesulfonamide;
N-(3,5-dichlorophenyl)-4-(piperazin-1-yl)benzenesulfonamide;
4-(piperazin-1-yl)-N-(5,6,7,8-tetrahydronaphthalen-2-yl)benzenesulfonamide;
N-(naphthalen-2-yl)-4-(piperazin-1-yl)benzenesulfonamide;
N-(cinnolin-7-yl)-4-(piperazin-1-yl)benzenesulfonamide;
N-(isoquinolin-7-yl)-4-(piperazin-1-yl)benzenesulfonamide;
4-(piperazin-1-yl)-N-(quinolin-6-yl)benzenesulfonamide;
N-(cinnolin-6-yl)-4-(piperazin-1-yl)benzenesulfonamide;
4-(piperazin-1-yl)-N-(quinoxalin-6-yl)benzenesulfonamide;
4-(piperazin-1-yl)-N-(pyrido[2,3-b]pyrazin-7-yl)benzenesulfonamide;
N-(1H-benzo[d][1,2,3]triazol-5-yl)-4-(piperazin-1-yl)benzenesulfonamide;
N-(2-methylbenzo[b]thiophen-5-yl)-4-(piperazin-1-yl)benzenesulfonamide;
N-(2-oxo-1,2,3,4-tetrahydroquinolin-7-yl)-4-(piperazin-1-yl)benzenesulfonamide;
N-(benzo[c][1,2,5]thiadiazol-5-yl)-4-(piperazin-1-yl)benzenesulfonamide;
N-(1H-indol-6-yl)-4-(piperazin-1-yl)benzenesulfonamide;
N-(1H-indol-5-yl)-4-(piperazin-1-yl)benzenesulfonamide;
N-(benzo[d]isoxazol-5-yl)-4-(piperazin-1-yl)benzenesulfonamide;
N-(2-aminoimidazo[1,2-a]pyrimidin-6-yl)-4-(piperazin-1-yl)benzenesulfonamide;
N-(2,3-dihydrobenzofuran-6-yl)-4-(piperazin-1-yl)benzenesulfonamide;
N-(2,3-dihydrobenzofuran-5-yl)-4-(piperazin-1-yl)benzenesulfonamide;
N-(2,2-difluorobenzo[d][1,3]dioxol-5-yl)-4-(piperazin-1-yl)benzenesulfonamide;
N-phenyl-4-(piperazin-1-yl)benzamide;
N-(cinnolin-7-yl)-4-(piperazin-1-yl)benzamide;
4-(piperazin-1-yl)-N-(5,6,7,8-tetrahydronaphthalen-2-yl)benzamide;
1-(4-(phenylsulfonyl)phenyl)piperazine;
1-(4-((4-chlorophenyl)sulfonyl)phenyl)piperazine;
4-((4-(piperazin-1-yl)phenyl)sulfonyl)phenol;
1-methyl-4-((4-(piperazin-1-yl)phenyl)sulfonyl)pyridin-2(1H)-one;
4-((4-(piperazin-1-yl)phenyl)sulfonyl)pyridin-2(1H)-one;
1-(4-(difluoro(phenyl)methyl)phenyl)piperazine;
1-(4-(difluoro(pyridin-3-yl)methyl)phenyl)piperazine;
3-(difluoro(4-(piperazin-1-yl)phenyl)methyl)phenol;
phenyl(4-(piperazin-1-yl)phenyl)methanone;
1-(4-benzylphenyl)piperazine;
1-(4-(benzyloxy)phenyl)piperazine;
1-(4-phenoxyphenyl)piperazine;
1-(4-(4-bromophenoxy)phenyl)piperazine;
1-(4-(4-(methylthio)phenoxy)phenyl)piperazine;
4-(4-(piperazin-1-yl)phenoxy)benzoic acid;
4-(4-(piperazin-1-yl)phenoxy)benzamide;
2-bromo-4-(4-(piperazin-1-yl)phenoxy)benzoic acid;
5-(4-(piperazin-1-yl)phenoxy)picolinamide;
1-(4-(3,4-difluorophenoxy)phenyl)piperazine;
1-(4-(3,4-dimethylphenoxy)phenyl)piperazine;
2-hydroxy-N-phenyl-4-(piperazin-1-yl)benzenesulfonamide;
4-(2-oxopiperazin-1-yl)-N-phenylbenzenesulfonamide;
2-fluoro-4-(2-oxopiperazin-1-yl)-N-phenylbenzenesulfonamide;
2-hydroxy-N-phenyl-4-(piperazin-1-yl)benzamide;
1-(4-(difluoro(phenyl)methyl)-3-fluorophenyl)piperazin-2-one;
2-(phenylsulfonyl)-5-(piperazin-1-yl)phenol;
N-phenyl-4-(piperazin-1-yl-2,2,6,6-$d_4$)benzenesulfonamide;
4-(4-phenoxyphenyl)piperidine;
4-(4-(cyclohexyloxy)phenyl)piperidine;
4-(4-((tetrahydro-2H-pyran-4-yl)oxy)phenyl)piperidine;
4-(4-(piperidin-4-yl)phenoxy)piperidine;
1-(4-(cyclohexyloxy)phenyl)piperazine;
1-(4-((tetrahydro-2H-pyran-4-yl)oxy)phenyl)piperazine;
1-(4-(piperidin-4-yloxy)phenyl)piperazine;
N-phenyl-4-(piperidin-4-yl)benzenesulfonamide;
4-(piperidin-4-yl)-N-(5,6,7,8-tetrahydronaphthalen-2-yl)benzenesulfonamide;
N-phenyl-4-(piperidin-4-yl)benzamide;
4-(4-(difluoro(phenyl)methyl)phenyl)piperidine;
phenyl(4-(piperidin-4-yl)phenyl)methanone;
2-ethyl-N-phenyl-4-(piperazin-1-yl)benzamide;
1-(4-phenoxyphenyl)piperazin-2-one;
1-(4-(4-fluorobenzyl)phenyl)piperazine;
6-(4-(piperazin-1-yl)phenoxy)pyrimidin-4(3H)-one;
4-((4-(piperazin-1-yl)phenyl)sulfonyl)morpholine;
1-(4-(pyrrolidin-1-ylsulfonyl)phenyl)piperazine;
1-(2-fluoro-4-(phenylsulfonyl)phenyl)piperazine;
4-(piperazin-1-yl)benzenesulfonamide;
N-methyl-4-(piperazin-1-yl)benzenesulfonamide;
N-cyclopropyl-4-(piperazin-1-yl)benzenesulfonamide;
N-isopropyl-4-(piperazin-1-yl)benzenesulfonamide;
N-((4-(piperazin-1-yl)phenyl)sulfonyl)acetamide;
N-(4-(piperazin-1-yl)phenyl)methanesulfonamide;
N-(4-(piperazin-1-yl)phenyl)ethanesulfonamide;
N-(4-(piperazin-1-yl)phenyl)benzenesulfonamide;
4-(piperazin-1-yl)-N-(pyridin-4-yl)benzenesulfonamide;
N-(4-(piperazin-1-yl)phenyl)ethanesulfonamide;
N-(4-(piperazin-1-yl)phenyl)benzenesulfonamide;
4-(piperazin-1-yl)-N-(pyridin-3-yl)benzenesulfonamide;
4-(piperazin-1-yl)-N-(pyridin-2-yl)benzenesulfonamide;
4-(piperazin-1-yl)-N-(thiazol-2-yl)benzenesulfonamide;
4-(piperazin-1-yl)-N-(quinolin-7-yl)benzenesulfonamide;
N-phenyl-6-(piperazin-1-yl)pyridine-3-sulfonamide;
N-phenyl-5-(piperazin-1-yl)pyridine-2-sulfonamide;
N-(3,5-difluorophenyl)-4-(piperazin-1-yl)benzenesulfonamide;
N-(2,3-dihydro-1H-inden-2-yl)-4-(piperazin-1-yl)benzenesulfonamide;
3-fluoro-4-(piperazin-1-yl)-N-(5,6,7,8-tetrahydronaphthalen-2-yl)benzenesulfonamide;

6-(piperazin-1-yl)-N-(5,6,7,8-tetrahydronaphthalen-2-yl)
    pyridine-3-sulfonamide;
5-(piperazin-1-yl)-N-(5,6,7,8-tetrahydronaphthalen-2-yl)
    pyridine-2-sulfonamide;
N-phenyl-4-(piperidin-4-yl)benzenesulfonamide;
4-(piperidin-4-yl)-N-(5,6,7,8-tetrahydronaphthalen-2-yl)
    benzenesulfonamide;
1-(4-phenoxyphenyl)piperazine-2,2,3,3,5,5,6,6-$d_8$;
and 1-(4-(4-fluorobenzyl)phenyl)piperazine-2,2,3,3,5,5,
    6,6-$d_8$;
or a pharmaceutical composition thereof.

In one embodiment, the present invention contemplates, a method, comprising: a) providing; i) a PCSK9 protein, wherein said protein comprises a binding site that induces allosteric modulation and a low density lipoprotein receptor binding site; ii) a small organic compound capable of binding said binding site, and selected from the group consisting of a compound of a phenylpiperazine scaffold of Formula I; iii) a plurality of hepatocyte cells comprising a population of low density lipoprotein receptors; b) binding said small organic compound to said binding site, wherein said small organic compound induces a conformational shift of said protein; c) modulating said population of said low density lipoprotein receptors by said conformational shift. In one embodiment the present invention contemplates a method, wherein said small organic compound induces a conformational change of the PCSK9 protein, such that the population of low density lipoprotein receptors is increased.

In one embodiment, the small organic compound is an allosteric inhibitor ligand wherein said small molecule ligand induces a conformational change of the PCSK9 protein, such that the population of low density lipoprotein receptors is increased. In one embodiment, the small organic compound is an allosteric inhibitor ligand wherein said modulating increases said population of said low density lipoprotein receptors measurable on the cell surface of said plurality of hepatocytes. In one embodiment, the conformational shift of said protein is selected from the group consisting of an induced fit shift and a biomechanical shift. In one embodiment the small molecule compound is an organic chemical compound. In one embodiment, the small organic compound is selected from the group consisting of a phenylpiperazine scaffold of Formula I. In one embodiment, the small organic compound is selected from the group consisting of a phenylpiperazine scaffold of Formula I, wherein one or more atoms are substituted with an isotope are also contemplated. Also provided are pharmaceutically acceptable salts, hydrates, solvates, tautomeric forms, and stereoisomers of these compounds selected from the group consisting of a phenylpiperazine scaffold of Formula I.

In one embodiment, the small organic compound is an allosteric inhibitor ligand wherein said small molecule ligand induces a conformational change of the PCSK9 protein, such that the population of low density lipoprotein receptors is increased. In one embodiment, the small organic compound is an allosteric inhibitor ligand wherein said modulating increases said population of said low density lipoprotein receptors measurable on the cell surface of said plurality of hepatocytes. In one embodiment, the conformational shift of said protein is selected from the group consisting of an induced fit shift and a biomechanical shift. In one embodiment the small molecule compound is an organic chemical compound. In one embodiment, the small organic compound is selected from the group comprising of:

N-phenyl-4-(piperazin-1-yl)benzenesulfonamide;
N-isopropyl-4-((4-(piperazin-1-yl)phenyl)sulfonamido)
    benzamide;
N-methyl-4-((4-(piperazin-1-yl)phenyl)sulfonamido)benzamide;
N-cyclopentyl-4-(piperazin-1-yl)benzenesulfonamide;
N-cyclohexyl-4-(piperazin-1-yl)benzenesulfonamide;
N-(3,4-dimethylphenyl)-4-(piperazin-1-yl)benzenesulfonamide;
N-(3,5-dimethylphenyl)-4-(piperazin-1-yl)benzenesulfonamide;
N-(3,5-dichlorophenyl)-4-(piperazin-1-yl)benzenesulfonamide;
4-(piperazin-1-yl)-N-(5,6,7,8-tetrahydronaphthalen-2-yl)
    benzenesulfonamide;
N-(naphthalen-2-yl)-4-(piperazin-1-yl)benzenesulfonamide;
N-(cinnolin-7-yl)-4-(piperazin-1-yl)benzenesulfonamide;
N-(isoquinolin-7-yl)-4-(piperazin-1-yl)benzenesulfonamide;
4-(piperazin-1-yl)-N-(quinolin-6-yl)benzenesulfonamide;
N-(cinnolin-6-yl)-4-(piperazin-1-yl)benzenesulfonamide;
4-(piperazin-1-yl)-N-(quinoxalin-6-yl)benzenesulfonamide;
4-(piperazin-1-yl)-N-(pyrido[2,3-b]pyrazin-7-yl)benzenesulfonamide;
N-(1H-benzo[d][1,2,3]triazol-5-yl)-4-(piperazin-1-yl)
    benzenesulfonamide;
N-(2-methylbenzo[b]thiophen-5-yl)-4-(piperazin-1-yl)
    benzenesulfonamide;
N-(2-oxo-1,2,3,4-tetrahydroquinolin-7-yl)-4-(piperazin-1-yl)benzenesulfonamide;
N-(benzo[c][1,2,5]thiadiazol-5-yl)-4-(piperazin-1-yl)
    benzenesulfonamide;
N-(1H-indol-6-yl)-4-(piperazin-1-yl)benzenesulfonamide;
N-(1H-indol-5-yl)-4-(piperazin-1-yl)benzenesulfonamide;
N-(benzo[d]isoxazol-5-yl)-4-(piperazin-1-yl)benzenesulfonamide;
N-(2-aminoimidazo[1,2-a]pyrimidin-6-yl)-4-(piperazin-1-yl)benzenesulfonamide;
N-(2,3-dihydrobenzofuran-6-yl)-4-(piperazin-1-yl)benzenesulfonamide;
N-(2,3-dihydrobenzofuran-5-yl)-4-(piperazin-1-yl)benzenesulfonamide;
N-(2,2-difluorobenzo[d][1,3]dioxol-5-yl)-4-(piperazin-1-yl)benzenesulfonamide;
N-phenyl-4-(piperazin-1-yl)benzamide;
N-(cinnolin-7-yl)-4-(piperazin-1-yl)benzamide;
4-(piperazin-1-yl)-N-(5,6,7,8-tetrahydronaphthalen-2-yl)
    benzamide;
1-(4-(phenylsulfonyl)phenyl)piperazine;
1-(4-((4-chlorophenyl)sulfonyl)phenyl)piperazine;
4-((4-(piperazin-1-yl)phenyl)sulfonyl)phenol;
1-methyl-4-((4-(piperazin-1-yl)phenyl)sulfonyl)pyridin-2
    (1H)-one;
4-((4-(piperazin-1-yl)phenyl)sulfonyl)pyridin-2(1H)-one;
1-(4-(difluoro(phenyl)methyl)phenyl)piperazine;
1-(4-(difluoro(pyridin-3-yl)methyl)phenyl)piperazine;
3-(difluoro(4-(piperazin-1-yl)phenyl)methyl)phenol;
phenyl(4-(piperazin-1-yl)phenyl)methanone;
1-(4-benzylphenyl)piperazine;
1-(4-(benzyloxy)phenyl)piperazine;
1-(4-phenoxyphenyl)piperazine;
1-(4-(4-bromophenoxy)phenyl)piperazine;
1-(4-(4-(methylthio)phenoxy)phenyl)piperazine;
4-(4-(piperazin-1-yl)phenoxy)benzoic acid;
4-(4-(piperazin-1-yl)phenoxy)benzamide;
2-bromo-4-(4-(piperazin-1-yl)phenoxy)benzoic acid;

5-(4-(piperazin-1-yl)phenoxy)picolinamide;
1-(4-(3,4-difluorophenoxy)phenyl)piperazine;
1-(4-(3,4-dimethylphenoxy)phenyl)piperazine;
2-hydroxy-N-phenyl-4-(piperazin-1-yl)benzenesulfonamide;
4-(2-oxopiperazin-1-yl)-N-phenylbenzenesulfonamide;
2-fluoro-4-(2-oxopiperazin-1-yl)-N-phenylbenzenesulfonamide;
2-hydroxy-N-phenyl-4-(piperazin-1-yl)benzamide;
1-(4-(difluoro(phenyl)methyl)-3-fluorophenyl)piperazin-2-one;
2-(phenylsulfonyl)-5-(piperazin-1-yl)phenol;
N-phenyl-4-(piperazin-1-yl-2,2,6,6-$d_4$)benzenesulfonamide;
4-(4-phenoxyphenyl)piperidine;
4-(4-(cyclohexyloxy)phenyl)piperidine;
4-(4-((tetrahydro-2H-pyran-4-yl)oxy)phenyl)piperidine;
4-(4-(piperidin-4-yl)phenoxy)piperidine;
1-(4-(cyclohexyloxy)phenyl)piperazine;
1-(4-((tetrahydro-2H-pyran-4-yl)oxy)phenyl)piperazine;
1-(4-(piperidin-4-yloxy)phenyl)piperazine;
N-phenyl-4-(piperidin-4-yl)benzenesulfonamide;
4-(piperidin-4-yl)-N-(5,6,7,8-tetrahydronaphthalen-2-yl)benzenesulfonamide;
N-phenyl-4-(piperidin-4-yl)benzamide;
4-(4-(difluoro(phenyl)methyl)phenyl)piperidine;
phenyl(4-(piperidin-4-yl)phenyl)methanone;
2-ethyl-N-phenyl-4-(piperazin-1-yl)benzamide;
1-(4-phenoxyphenyl)piperazin-2-one;
1-(4-(4-fluorobenzyl)phenyl)piperazine;
6-(4-(piperazin-1-yl)phenoxy)pyrimidin-4(3H)-one;
4-((4-(piperazin-1-yl)phenyl)sulfonyl)morpholine;
1-(4-(pyrrolidin-1-ylsulfonyl)phenyl)piperazine;
1-(2-fluoro-4-(phenylsulfonyl)phenyl)piperazine;
4-(piperazin-1-yl)benzenesulfonamide;
N-methyl-4-(piperazin-1-yl)benzenesulfonamide;
N-cyclopropyl-4-(piperazin-1-yl)benzenesulfonamide;
N-isopropyl-4-(piperazin-1-yl)benzenesulfonamide;
N-((4-(piperazin-1-yl)phenyl)sulfonyl)acetamide;
N-(4-(piperazin-1-yl)phenyl)methanesulfonamide;
N-(4-(piperazin-1-yl)phenyl)ethanesulfonamide;
N-(4-(piperazin-1-yl)phenyl)benzenesulfonamide;
4-(piperazin-1-yl)-N-(pyridin-4-yl)benzenesulfonamide;
N-(4-(piperazin-1-yl)phenyl)ethanesulfonamide;
N-(4-(piperazin-1-yl)phenyl)benzenesulfonamide;
4-(piperazin-1-yl)-N-(pyridin-3-yl)benzenesulfonamide;
4-(piperazin-1-yl)-N-(pyridin-2-yl)benzenesulfonamide;
4-(piperazin-1-yl)-N-(thiazol-2-yl)benzenesulfonamide;
4-(piperazin-1-yl)-N-(quinolin-7-yl)benzenesulfonamide;
N-phenyl-6-(piperazin-1-yl)pyridine-3-sulfonamide;
N-phenyl-5-(piperazin-1-yl)pyridine-2-sulfonamide;
N-(3,5-difluorophenyl)-4-(piperazin-1-yl)benzenesulfonamide;
N-(2,3-dihydro-1H-inden-2-yl)-4-(piperazin-1-yl)benzenesulfonamide;
3-fluoro-4-(piperazin-1-yl)-N-(5,6,7,8-tetrahydronaphthalen-2-yl)benzenesulfonamide;
6-(piperazin-1-yl)-N-(5,6,7,8-tetrahydronaphthalen-2-yl)pyridine-3-sulfonamide;
5-(piperazin-1-yl)-N-(5,6,7,8-tetrahydronaphthalen-2-yl)pyridine-2-sulfonamide;
N-phenyl-4-(piperidin-4-yl)benzenesulfonamide;
4-(piperidin-4-yl)-N-(5,6,7,8-tetrahydronaphthalen-2-yl)benzenesulfonamide;
1-(4-phenoxyphenyl)piperazine-2,2,3,3,5,5,6,6-$d_8$;
and 1-(4-(4-fluorobenzyl)phenyl)piperazine-2,2,3,3,5,5,6,6-$d_8$;
or a pharmaceutical composition thereof.

In one embodiment, the present invention contemplates a compound including, but not limited to, a phenylpiperazine scaffold of Formula I. In one embodiment, the PCSK9 binding small organic ligand is selected from the group consisting of: a phenylpiperazine scaffold of Formula I. In one embodiment, the compound is formulated as a pharmaceutical composition. In one embodiment, the pharmaceutical composition further comprises a pharmaceutical drug. In one embodiment, the pharmaceutical drug is selected from the group consisting of a statin, a cardiovascular drug, a metabolic drug, and an antihypertensive drug. In one embodiment, the pharmaceutical drug is selected from the group consisting of ezetimibe, amlodipine besylate, sitagliptin, metformin, atorvastatin, rosuvastatin and simvastatin. In one embodiment, the pharmaceutical composition is formulated as selected from the group consisting of a tablet, a liquid, a gel, a capsule, a sachet, a microparticle, a liposome, a nanoparticle, a salt, a transdermal patch, an ointment, a lotion, a cream, a gel, a drop, a strip, a suppository, a spray and a powder.

In one embodiment, the present invention contemplates a composition comprising a PCSK9 allosteric small organic compound selected from the group consisting of a phenylpiperazine scaffold of Formula I as a small molecule ligand. In one embodiment, the composition is a pharmaceutical composition. In one embodiment, the pharmaceutical composition comprises an effective dose of said ligand. In one embodiment, the pharmaceutical composition comprises salts. In one embodiment, the pharmaceutical composition is formulated for oral administration.

In one embodiment, the present invention contemplates a method, comprising: a) administering to a subject a small organic compound selected from the group consisting of a phenylpiperazine scaffold of Formula I, which binds PCSK9 and is an allosteric modulator of the protein, wherein said subject has at least one symptom of a cardiovascular disease; and b) reducing said at least one symptom of cardiovascular disease by said PCSK9 allosteric modulator small molecule compound administration. In one embodiment, said at least one symptom is reduced between 10%-85%. In one embodiment, said at least one symptom is reduced between 20%-65%. In one embodiment, said at least one symptom is reduced between 30%-55%. In one embodiment, the cardiovascular disease comprises a coronary disease. In one embodiment, the cardiovascular disease comprises hypertension. In one embodiment, the cardiovascular disease comprises hypercholesterolemia. In one embodiment, the cardiovascular disease comprises atherosclerosis. In one embodiment, the at least one symptom comprises reduced circulating high density lipoprotein. In one embodiment, the at least one symptom comprises elevated circulating cholesterol. In one embodiment, the at least one symptom comprises elevated circulating low density lipoprotein. In one embodiment, the at least one symptom comprises high blood pressure. In one embodiment, the administering comprises an effective dose of said PCSK9 allosteric modulator small organic compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the allosteric modulator small organic compound is an organic chemical compound small molecule. In one embodiment, the small organic compound is selected from the group consisting of a phenylpiperazine scaffold of Formula I.

In one embodiment, the present invention contemplates a method, comprising: a) administering a PCSK9 allosteric small organic compound selected from the group consisting of a phenylpiperazine scaffold of Formula I to a subject, wherein said subject has at least one symptom of a liver disease; and b) reducing said at least one symptom of liver disease by said PCSK9 allosteric small molecule administration. In one embodiment, the at least one symptom comprises elevated low density lipoprotein receptor density. In one embodiment the at least one symptom comprises reduced low density lipoprotein receptor density. In one embodiment, said at least one symptom is reduced between 10%-85%. In one embodiment, said at least one symptom is reduced between 20%-65%. In one embodiment, said at least one symptom is reduced between 30%-55%. In one embodiment, the PCSK9 allosteric small organic compound comprises a PCSK9 allosteric inhibitor compound. In one embodiment, the administering comprises an effective dose of said PCSK9 allosteric inhibitor compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the small organic compound is an organic chemical compound small molecule. In one embodiment, the small organic compound is selected from the group consisting of a phenylpiperazine scaffold of Formula I In one embodiment, the present invention contemplates a method, comprising: a) administering a PCSK9 allosteric small organic compound selected from the group consisting of a phenylpiperazine scaffold of Formula I to a subject, wherein said subject has at elevated PCSK9 protein levels in the blood; and b) reducing said at least one symptom of elevated PCSK9 by said PCSK9 allosteric small molecule compound administration. In one embodiment, the at least one symptom comprises reduced low density lipoprotein receptor density. In one embodiment, said at least one symptom is reduced between 10%-85%. In one embodiment, said at least one symptom is reduced between 20%-65%. In one embodiment, said at least one symptom is reduced between 30%-55%. In one embodiment, the PCSK9 allosteric small molecule compound comprises a PCSK9 allosteric inhibitor compound. In one embodiment, the administering comprises an effective dose of said PCSK9 allosteric small molecule compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the small molecule compound is an organic chemical compound. In one embodiment, the small organic compound is selected from the group consisting of a phenylpiperazine scaffold of Formula I.

In one embodiment, the present invention contemplates a method, comprising: a) administering a PCSK9 allosteric small organic compound selected from the group consisting of a phenylpiperazine scaffold of Formula I to a subject, wherein said subject has at below-average PCSK9 protein levels in the blood; and b) reducing said at least one symptom of elevated PCSK9 by said PCSK9 allosteric small molecule compound administration. In one embodiment, the at least one symptom comprises elevated low density lipoprotein receptor density. In one embodiment, said at least one symptom is reduced between 10%-85%. In one embodiment, said at least one symptom is reduced between 20%-65%. In one embodiment, said at least one symptom is reduced between 30%-55%. In one embodiment, the PCSK9 allosteric small molecule compound comprises a PCSK9 allosteric activator compound. In one embodiment, the administering comprises an effective dose of said PCSK9 allosteric small molecule compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the small molecule compound is an organic chemical compound. In one embodiment, the small organic compound is selected from the group consisting of a phenylpiperazine scaffold of Formula I.

In one embodiment, the present invention further contemplates a kit comprising (a) a first container comprising a pharmaceutical composition of a small organic compound of Formula I; and (b) instructions for the use thereof for treatment of hypercholesterolemia. In one embodiment, the present invention further contemplates a kit comprising (a) first container comprising a pharmaceutical composition of a small organic compound of Formula I; and (b) instructions for the use thereof for inhibition of PCSK9 protein biological activity.

In one embodiment, the present invention further contemplates a small organic compound of Formula I for use in treating hypercholesterolemia. In one embodiment, the present invention further contemplates a small organic compound of Formula I for use in lowering serum LDL levels.

In one embodiment, the present invention further contemplates a method for reducing LDL levels in a mammal comprising administering a pharmaceutical composition of a small organic compound of Formula I to the mammal. In one embodiment, the present invention further contemplates a method for reducing LDL levels in a patient comprising administering a pharmaceutical composition of a small organic compound of Formula I to the patient.

In one embodiment, the present invention further contemplates a method for treating hypercholesterolemia in a mammal comprising administering a pharmaceutical composition of a small organic compound of Formula I to the mammal. In one embodiment, the present invention further contemplates a method for treating hypercholesterolemia in a patient comprising administering a pharmaceutical composition of a small organic compound of Formula I to the patient.

In one embodiment, the present invention further contemplates a method for reducing cholesterol levels in a patient in need thereof, wherein said method comprises identifying a patient with elevated serum cholesterol levels, and administering a pharmaceutical composition of a small organic compound of Formula I to the patient. In one embodiment, the present invention further contemplates a method for reducing LDL levels in a patient in need thereof, wherein said method comprises identifying a patient with elevated serum LDL levels, and administering a pharmaceutical composition of a small organic compound of Formula I to the patient. In one embodiment, the present invention further contemplates a method for treating hypercholesterolemia in a patient in need thereof, wherein said method comprises identifying a patient with elevated serum LDL levels, and administering a pharmaceutical composition of a small organic compound of Formula I to the patient.

Definitions

The Following Abbreviations are Used Throughout the Specification:
Bn: benzyl
Bz: benzoyl
Ac: acetyl
Boc: tert-butoxycarbonyl
Fmoc: 9-fluorenylmethoxycarbonyl
Cbz: benzyloxycarbonyl
TFA: trifluoroacetic acid
NMP: N-methylpyrrolidone
PyBOP: (benzotriazol-1-yloxy)tripyrrolidinophosphoniumhexafluorophosphate
NMM: N-methyl morpholine
HPLC: high pressure liquid chromatography
THF: tetrahydrofuran
DMSO: dimethylsulfoxide
DMF: N,N-dimethylformamide
TMS-Br: trimethylsilyl bromide
Tf: trifluoromethylsulfonyl
HATU: 2-(7-aza-1H-benzotriazole-1-yl)-1,1,3,3-tetramethyluroniumhexafluorophosphate
DIPEA: diisopropylethylamine
DCM: dichloromethane The terms "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "hydrate" refers to the complex formed by the combining of a compound of Formula I and water.

The term "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid, and ethanolamine.

The term "small molecule compound" as used herein, refers to an exogenously synthesized organic chemical compound of less than 1,000 Da.

The term "small molecule ligand" as used herein, refers to a small molecule compound that is bound by another naturally occurring biomolecule to form a complex.

The term "small organic compound" as used herein, refers to a small molecule compound, and is synonymous with "organic compound" and "small molecule".

The term "small organic compound ligand" as used herein refers to a small organic compound that is bound by another naturally occurring biomolecule to form a complex.

The term "conformation" as used herein, refers to a three-dimensional stereochemical configuration of any compound and/or molecule. For example, any specific conformation results from a thermodynamic balance between steric interactions, hydrophobic interactions, hydrogen bonding, electrochemical bonding and/or salt bridge interactions in a protein.

The term "LDL-R" and "LDLR" as used herein, refers to an abbreviation for the low density lipoprotein receptor. The abbreviation may be in reference to the entire LDL-R receptor protein or any portion thereof. LDL-Rs reside on a cell surface and can bind to low density lipoproteins such that the LDL-R/LDL complex become internalized within a cell (i.e., for example, a hepatocyte), wherein the LDL is released and the LDL-R is recycled back to the cell surface.

The term, "binding interface" as used herein, refers to any collection of attractive interactions (i.e., for example, hydrogen bonding, electrostatic interactions, hydrophobic interactions, etc) between the functional groups (i.e., for example, hydroxyl, amide, amine, carboxyl, amidine, guanidine, hydrocarbon, sulfonyl etc.) of at least two different molecules. The collection of attractive forces forms a stable molecular plane thereby forming a 'binding interface' between the at least two molecules.

The term "induced fit" as used herein, refers to any acceptance of a small molecule compound requiring a change in the receiving molecule's conformation. Such a conformation may be facilitated by a translational/rotational movement of amino acid side chains and flexible loops, thereby rearranging the electrostatic and/or hydrophobic fields.

The term "complex" or "composition" as used herein, refers to any chemical association of two or more ions or molecules joined usually by weak electrostatic bonds rather than by covalent bonds. For example, a complex or composition may be formed between a small molecule compound as described herein and a PCSK9 amino acid sequence, thereby creating a small molecule compound: PCSK9 amino acid sequence complex or composition. Optionally, such complexes or compositions may also include, but are not limited to, an LDLR amino acid sequence or any portion thereof, including but not limited to the EGFA region.

The term "hydrogen bond" as used herein, an electrostatic attraction between a hydrogen atom in one polar molecule (as of water) and a small electronegative atom (as of oxygen, nitrogen, or fluorine) in usually another molecule of the same or a different polar substance.

The term "salt bridge" as used herein, refers to any interaction or a combinations of interactions, such as hydrogen bonding and/or electrostatic interactions, which align cationic and anionic chemical structures in such a way that the charged moieties overlap.

The term "interaction" as used herein, refers to any effect that one molecule and/or functional group may have on another molecule and/or functional group. Such effects may include, but are not limited to, steric (i.e., for example, physical), electrostatic (i.e., for example, electrical attraction or repulsion), electromagnetic, hydrophilic, or hydrophobic effects.

The term "overlap" as used herein, refers to any positioning of molecules in such a way that the electronic structure of one molecule is on top of, and extending past the border of another molecule, or be positioned in this way.

The term "hypercholesterolemia" as used herein, refers to any medical condition wherein blood cholesterol levels are elevated above the clinically recommended levels. For example, if cholesterol is measured using low density lipoproteins (LDLs), hypercholesterolemia may exist if the measured LDL levels are above, for example, approximately 75 mg/dl. Alternatively, if cholesterol is measured using free plasma cholesterol, hypercholesterolemia may exist if the measured free cholesterol levels are above, for example, approximately 200-220 mg/dl.

The term "hypocholesterolemia" as used herein, refers to any medical condition wherein blood cholesterol levels are below clinically recommended levels. For example, if total cholesterol or LDL-C levels are measured as below the $5^{th}$ percentile of the general population after adjustment for gender, race, and age.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" and/or "disorder", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The term "affinity" as used herein, refers to the measure of the thermodynamic tendency of two or more molecules to assemble to form a multi-part complex and to remain assembled in said complex. For example, a small molecule ligand has a high affinity for PCSK9 and is thermodynamically favored to form a complex. It is understood that a change in conditions (e.g., pH during the receptor internalization process) may reduce the affinity of the molecules such that they dissociate, or separate, from one another. For example, pH changes can result in a decrease in the LDL affinity for LDLR and subsequent dissociation of that complex.

The term "derived from" as used herein, refers to the source of a compound. In one respect, a compound may be derived from an organism or particular species. In another respect, a compound may be derived from a larger complex. In another respect, a compound may be derived by chemical modification of part or all of a larger complex.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur, and forming a contiguous protein backbone. In general, a protein comprises amino acids having an order of magnitude within the hundreds.

The term "peptide" as used herein, refers to any of various amides that are derived from three or more amino acids by combination of the amino group of one acid with the carboxyl group of another and are usually obtained by partial hydrolysis of proteins. In general, a peptide comprises amino acids having an order of magnitude within the tens or smaller.

The term, "purified" or "isolated", as used herein, may refer to a composition that has been subjected to treatment (i.e., for example, fractionation) to remove various other components, and which composition substantially retains its expressed biological activity.

As used herein, the term "substantially purified" refers to molecules, such as small molecule compound, that are removed from their normal environment, isolated or separated, and are at least 60% free, preferably 75% free, and more preferably 90% free from other components with which they are normally associated.

The term "purified to homogeneity" is used to include compositions that have been purified to 'apparent homogeneity" such that there is single small molecule compound species (i.e., for example, based upon SDS-PAGE or HPLC analysis). A purified composition is not intended to mean that all trace impurities have been removed.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The terms "amino acid sequence" and "polypeptide sequence" as used herein, are interchangeable and to refer to a contiguous sequence of multiple amino acids.

The term "derivative" as used herein, refers to any chemical modification of a small molecule compound. Examples of such modifications would include, but are not limited to, replacement of a hydrogen by an alkyl, aryl, hydroxyl, sulfhydryl, sulfoxyl, sulfonyl, acyl, phosphoryl, alkoxyl, amino or amino heterocyclic group. Other possible chemical modification might include, but are not limited to, C-terminal amides, and acyl or sulfonyl N-terminal modifications.

The term "bind" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte/target being measuring/affected. The "binding" interaction may be brief as in the situation where binding causes a chemical reaction to occur. That is typical when the binding component is an enzyme and the analyte/target is a substrate for the enzyme. Reactions resulting from contact between the binding agent and the analyte/target are also within the definition of binding for the purposes of the present invention.

Chemical Terminology:

Alkyl: a chain consisting of only carbon and hydrogen atoms such that each carbon atom directly connects to exactly 4 different atoms, using only single bonds.

Lower alkyl: an alkyl chain containing 1-6 carbon atoms.

Branched alkyl: an alkyl chain containing one or more carbon atoms which are directly connected to more than 2 other carbon atoms without creating a ring of carbon atoms.

Hydroxyalkyl: an alkyl chain where at least one carbon atom is bonded to a hydroxyl, that is, —OH.

Cycloalkyl: an alkyl chain forming a ring. Examples would include -cyclopropyl or -cyclohexyl.

Heterocycle: a chain of atoms forming a ring and containing one or more "heteroatoms"; that is, atoms other than C or H able to form stable covalent bonds, such as N, O, or S. In this context, "heterocycle" will imply a non-aromatic ring. Examples include a tetrahydrofuran ring, with 4 carbon atoms and one oxygen, or a morpholine, with 4 carbon atoms and one nitrogen and one oxygen arranged such that the N and O are 1,4 to one another.

Aromatic ring: a ring of atoms containing alternating single and double "pi" bonds such that the number pi electrons (typically 2 per double bonds for stable compounds) is an even number but not a multiple of four.

Acyl: a carbonyl containing radical: —CO—R. In this document, R=affords a typical peptide modifying group, such as: —$CH_3$ (acetyl), —$CH(CH_2)_2$ (isobutyryl).

Benzoyl: a carbonyl containing radical: —CO-Ph, where Ph=phenyl.

Sulfonyl: a sulfonyl containing radical: —$SO_2$—R.

Carbamoyl: a radical: —$CONR_1R_2$

Alkoxy: an alkyl chain containing one or more ether (—O—) linkages, such as: —$CH_2CH_2OCH_3$.

Aryl: phenyl or substituted phenyl

Heteroaryl: a 5 or 6 membered aromatic heterocycle

Fused heterocyle: a ring system, such as indole, containing two or more fused rings, of which at least one is a heterocycle. The rings need not be aromatic: indoline has an aromatic ring fused to a non-aromatic ring.

Negatively charged polar group: A polar group carrying a negative charge at physiologic pH.

DETAILED DESCRIPTION OF THE INVENTION

Figure 1:
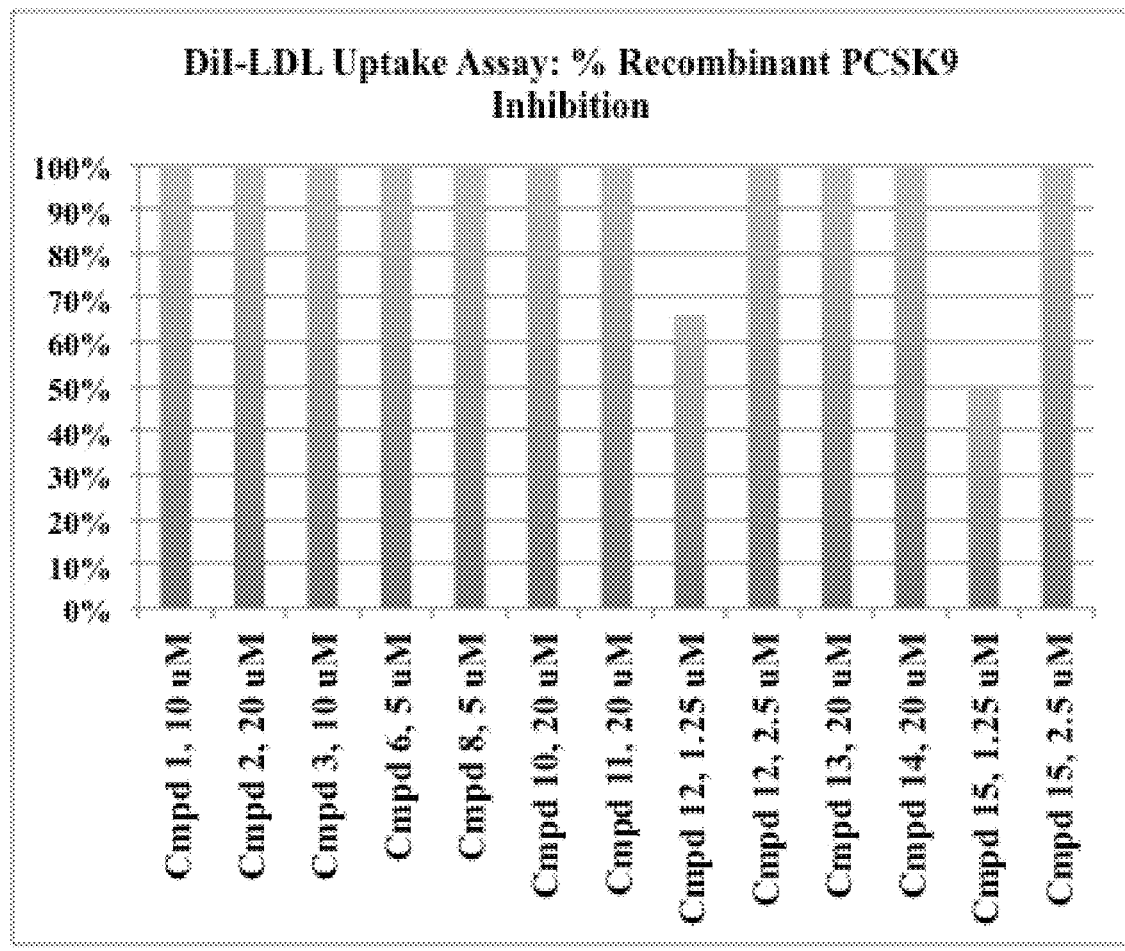
FIG. 1 shows exemplary data of % PCSK9 modulation in HepG2 cells in a DiI-LDL Uptake Assay. The cells were incubated in a 96-well plate for a total of 16 h in the absence or presence of recombinant PCSK9 (final concentration 2.5 ug/ml) protein alone or recombinant PCSK9 protein pre-mixed with indicated concentration of experimental compounds (Cmpd #). After 16 h, DiI-LDL (final concentration 5 ug/ml) was added to the incubation mixtures. After 4 h, cells are stained with Hoechst 33342 for 30 minutes, then rinsed with phosphate buffered saline, and then a final volume of 100 ul phosphate buffered saline was added to each well. The fluorescence was measured (DiI: excitation at 550 nm and emission at 590 nm; Hoechst: excitation at 355 nm, emission at 460 nm). The percent recombinant PCSK9 inhibition was calculated as ['Compound Dose DiI Fluorescence'–'2.5 ug/ml PCSK9-treated DiI Fluorescence']/['No PCSK9 DiI Fluorescence'–'2.5 ug/ml PCSK9-treated DiI Fluorescence']×100%.
Figure 2:
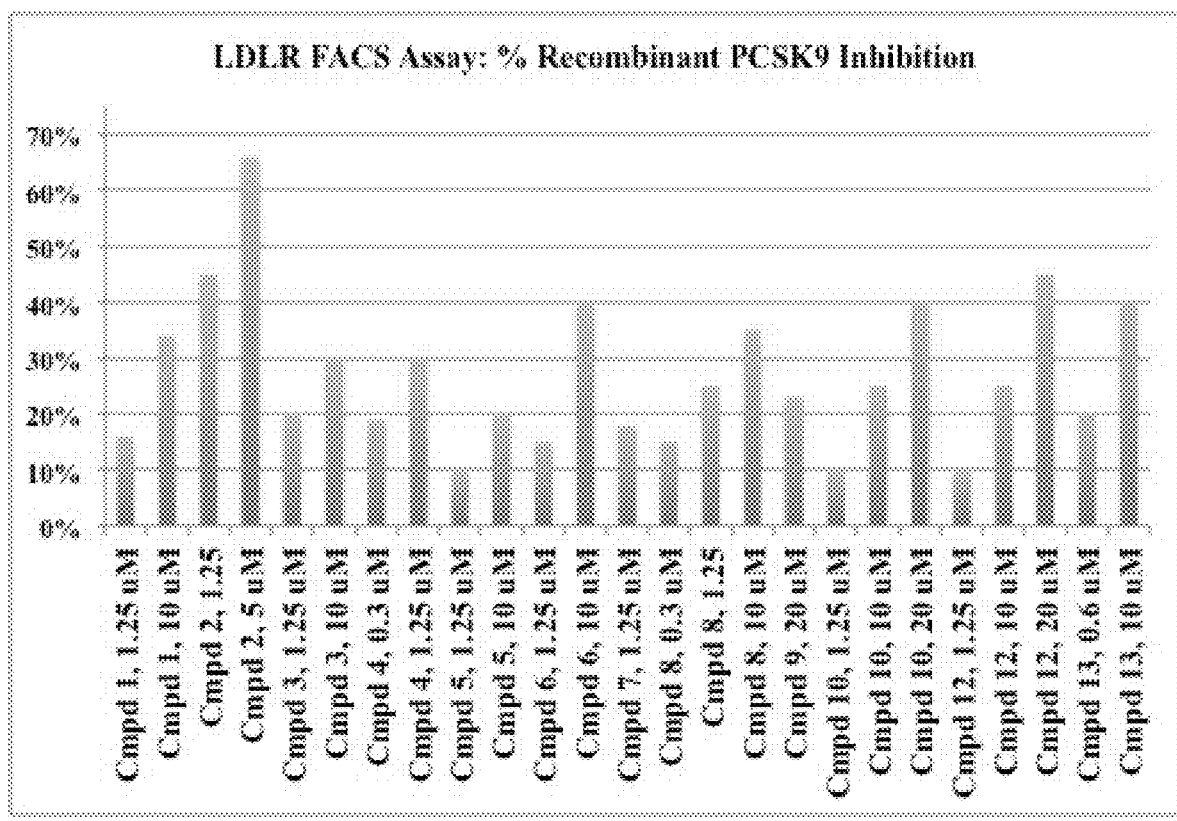
FIG. 2 shows exemplary data of % PCSK9 inhibition in HuH7 cells in an LDLR FACS Assay. The cells were incubated in 24-well plates for a total of 6 h in the absence or presence of recombinant PCSK9 protein (final concentration of 5.0 ug/ml), or in the presence of PCSK9 protein mixed with indicated concentration of experimental compound (Cmpd #). After 6 hours, the cells were released from the plate, stained with anti-LDLR antibody, then rinsed, counterstained with DAPI, and then measured by fluorescence activated cell sorting (FACS). The percent recombinant PCSK9 inhibition was calculated as ['Compound Dose LDLR Fluorescence'–'5.0 ug/ml PCSK9-treated LDLR Fluorescence']/['No PCSK9 Basal LDLR Fluorescence'–'5.0 ug/ml PCSK9-treated LDLR Fluorescence']×100%.

This invention is related to the field of PCSK9 biology and use of compounds for treatment including conditions of hypercholesterolemia and hypocholesterolemia. In particular, the invention provides compositions of ligands that bind and alter PCSK9 biological conformation and activity. These ligands are small molecule chemical compounds, and more preferably small molecule compounds less than 800 Da. Altering the conformation of PCSK9 can change the interactions between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for ligands that can raise LDL levels.

I. Physiological Role of Native PCSK9

Proprotein convertase subtilisin/kexin type 9, also known as PCSK9, is an enzyme that in humans is encoded by the PCSK9 gene. Seidah et al., "The secretory proprotein convertase neural apoptosis-regulated convertase 1 (NARC-1): liver regeneration and neuronal differentiation" *Proc. Natl. Acad. Sci. U.S.A.* 100 (3): 928-933 (2003). Similar genes (orthologs) are found across many species. Many enzymes, including PSCK9, are inactive when they are first synthesized, because they have a section of peptide chains that blocks their activity; proprotein convertases remove that section to activate the enzyme.

The PSCK9 gene encodes a proprotein convertase belonging to the proteinase K subfamily of the secretory subtilase family. The encoded protein is synthesized as a soluble zymogen that undergoes autocatalytic intramolecular processing in the endoplasmic reticulum. The protein may function as a proprotein convertase. For example, a human PCSK9 amino acid sequence is:

001 mgtvssrrsw wplplllllll lllgpagara qededgdyee lvlalrseed glaeapehgt 061 tatfhrcakd pwrlpgtyvv vlkeethlsq sertarrlqa qaarrgyltk ilhvfhgllp 121 gflvkmsgdl lelalklphv dyieedssvf aqsipwnler itppryrade yqppdggslv 181 evylldtsiq sdhreiegry mvtdfenvpe edgtrfhrqa skcdshgthl agvvsgrdag 241 vakgasmrsl rvincqgkgt vsgtliglef irksqlvqpv gplvvllpla ggysrvlnaa 301 cqrlaragvv lvtaagnfrd daclyspasa pevitvgatn aqdqpvtlgt lgtnfgrcvd 361 lfapgediig assdcstcfv sqsgtsqaaa hvagiaamml saepeltlae lrqrlihfsa 421 kdvineawfp edqrvltpnl vaalppsthg agwqlfcrtv wsahsgptrm atavarcapd 481 eellscssfs rsgkrrgerm eaqggklvcr ahnafggegv yaiarccllp qancsvhtap 541 paeasmgtrv hchqqghvlt gcsshweved lgthkppvlr prgqpnqcvg hreasihasc 601 chapgleckv kehgipapqe qvtvaceegw tltgcsalpg tshvlgayav dntcvvrsrd 661 vsttgstseg avtavaiccr srhlaqasqe lq (Accession No. NP 777596).

PSCK9 is believed to play a regulatory role in cholesterol homeostasis. For example, PCSK9 can bind to the epidermal growth factor-like repeat A (EGF-A) domain of the low-density lipoprotein receptor (LDL-R) resulting in LDL-R internalization and degradation. Clearly, it would be expected that reduced LDL-R levels result in decreased metabolism of LDL-C, which could lead to hypercholesterolemia.

As it is estimated that approximately 9 million Americans have a high or very high risk for heart-related problems that could benefit from PCSK9 inhibitors (especially when in combination with statins). PCSK9 inhibitors could result in such widespread usage having the potential to replace statins in certain conditions. PCSK9 has medical significance because it acts in cholesterol homeostasis. Drugs that block PCSK9 biological actions are believed to lower circulating low-density lipoprotein cholesterol (LDL-C) levels (i.e., for example, by increasing the availability of LDL-Rs and, consequently, LDL-C clearance). Such drugs are beginning Phase III clinical trials to assess their safety and efficacy in humans, and to determine if they can improve outcomes in heart disease.

Drugs that inhibit LDL-R/PCSK9 complex formation have been suggested to lower cholesterol much more than conventionally available cholesterol-lowering drugs (i.e., for example, statins). It is biologically plausible that this would also lower heart attacks and other diseases caused by raised cholesterol. Studies with humans, including phase III clinical trials now underway, are focused as to whether PCSK9 inhibition actually does lower cardiovascular disease, with acceptable side effects. Lopez D., "Inhibition of PCSK9 as a novel strategy for the treatment of hypercholesterolemia" *Drug News Perspect.* 21(6): 323-e30 (2008); Steinberg et al., "Inhibition of PCSK9: a powerful weapon for achieving ideal LDL cholesterol levels" *Proc. Natl. Acad. Sci. U.S.A.* 106(24): 9546-9547 (2009); Mayer, "Annexin A2 is a C-terminal PCSK9-binding protein that regulates endogenous low density lipoprotein receptor levels" *J. Biol. Chem.* 283(46): 31791-31801 ((2008); and anonymous, "Bristol-Myers Squibb selects Isis drug targeting PCSK9 as development candidate for prevention and treatment of cardiovascular disease" *Press Release. FierceBiotech.* 2008-04-08.

Currently, it has been reported that PCSK9 antibody drugs are in clinical trials (e.g., for example, Sanofi/Regeneron, Amgen, Pfizer, Novartis, Roche). However, one disadvantage of antibody therapy is that the administration is performed by subcutaneous or intravenous injection. A number of monoclonal antibodies that bind to PCSK9 near the catalytic domain that interact with the LDL-R and hence inhibit LDL-R/PCSK9 complex formation are currently in clinical trials. These antibodies include AMG145 (Amgen), 1D05-IgG2 (Merck & Co.), and SAR236553/REGN727 (Aventis/Regeneron). Lambert et al., "The PCSK9 decade" *J. Lipid Res.* 53(12): 2515-2524 (2012).

Peptides that mimic the EGF-A domain of the LDL-R have been developed to inhibit LDL-R/PCSK9 complex formation. Shan et al., "PCSK9 binds to multiple receptors and can be functionally inhibited by an EGF-A peptide". *Biochem. Biophys. Res. Commun.* 375(1): 69-73 (2008). Peptidic PCSK9 inhibitors of the EGF-A binding site were identified by screening both linear and disulfide-constrained phage-displayed peptide libraries. This approach identified a 13-amino acid peptide (Pep2-8) that includes structural mimicry of the natural binding domain of LDL receptor. The peptide inhibitor binding site was determined to largely overlap with that of the EGF(A) domain; therefore, Pep2-8 acts a competitive inhibitor of LDL receptor binding. This is akin to the inhibition mechanism of anti-PCSK9 monoclonal antibodies, which also disrupt the interaction of the LDL receptor-EGF(A) domain with PCSK9. Zhang et al., "Identification of a Small Peptide That Inhibits PCSK9 Protein Binding to the Low Density Lipoprotein Receptor' *J Biol Chem* 289:942-955 (2014).

PCSK9 antisense oligonucleotides (Isis Pharmaceuticals) have been shown to increase expression of the LDL-R and decrease circulating total cholesterol levels in mice. Graham et al., "Antisense inhibition of proprotein convertase subtilisin/kexin type 9 reduces serum LDL in hyperlipidemic mice" *J. Lipid Res.* 48(4): 763-767 (2007). It has also been reported that a locked nucleic acid (Santaris Pharma) reduced PCSK9 mRNA levels in mice. Gupta et al., "A locked nucleic acid antisense oligonucleotide (LNA) silences PCSK9 and enhances LDLR expression in vitro and in vivo" *PLoS ONE* 5(5): e10682 (2010); and Lindholm et al., "PCSK9 LNA antisense oligonucleotides induce sustained reduction of LDL cholesterol in nonhuman primates". *Mol. Ther.* 20(2):376-381 (2012). Initial clinical trials of an RNAi (ALN-PCS, Alnylam Pharmaceuticals) has shown positive results as an effective means of inhibiting LDL-R/PCSK9 complex formation. Frank-Kamenetsky et al., "Therapeutic RNAi targeting PCSK9 acutely lowers plasma cholesterol in rodents and LDL cholesterol in nonhuman primates" *Proc. Natl. Acad. Sci. U.S.A.* 105(33): 11915-11920 (2008).

II. PCSK9 Allosteric Site Modulation Small Molecule Compounds

Variants of PCSK9 can reduce or increase circulating cholesterol. Abifadel et al., "Mutations in PCSK9 cause autosomal dominant hypercholesterolemia" *Nat. Genet.* 34(2): 154-156 (2003). LDL-C is normally removed from the blood when it binds to an LDL-R on the surface of liver cells, and is internalized within the hepatocyte as a receptor-ligand complex. However, when PCSK9 binds to an LDL-R, the LDL-R is concomitantly degraded along with the complexed LDL particle. However, if a PCSK9 is not bound to an LDL-R, the LDL-R is recycled after internalization thereby returning to the surface of the cell for removal of more cholesterol.

In some embodiments, the invention relates to small organic compounds having a modulation effect on PCSK9's ability to form an LDL-R/PCSK9 complex. In some embodiments, the present invention contemplates the use of small organic compounds that bind to a PCSK9 protein and modulate the protein's biological activity. In some embodiments, the small molecules decrease LDL-R/PCSK9 complex formation and are thereby useful to treat various diseases comprising lipid dysregulation. In some embodiments, the small molecules increase LDL-R/PCSK9 complex formation and are thereby useful in research and development of therapies relevant to LDL dysregulation.

Although it is not necessary to understand the mechanism of an invention, it is believed that "gain-of-function" (GOF) PCSK9 mutants may result in conditions including, but not limited to, hypercholesterolemia. For example, compounds that bind to a PCSK9 and increase the affinity of PCSK9's low density lipoprotein receptor for a low density lipoprotein receptor on the surface of a cell (e.g., a hepatocyte) would be expected to increase the symptoms of hypercholesterolemia by increasing low density lipoprotein receptor internalization and degradation.

Although it is not necessary to understand the mechanism of an invention, it is believed that "loss-of-function" (LOF) PCSK9 mutants may result in conditions comprising reduced low density lipoproteins and would be expected to result in hypocholesterolemia thereby reducing the risk of cardiovascular diseases, including but not limited to, coronary heart disease. For example, small molecule compounds that bind to a PCSK9 that decrease the affinity of PCSK9's low density lipoprotein receptor binding site for a low density lipoprotein receptor on the surface of a cell (e.g., a hepatocyte) would be expected to reduce the symptoms of hypercholesterolemia by promoting low density lipoprotein internalization and clearance due to concomitant recycling of the low density lipoprotein receptor.

The presently disclosed embodiments of PCSK9 binding small organic compounds have several advantages over current peptides and ligands described in the art. For example, small molecule PCSK9 binding compounds, as contemplated herein, have the advantage that these compounds are smaller than many previously described peptides. It is envisioned that these small organic compounds can be administered orally without immunological reactions seen with antibody administration, or systemic degradation problems as seen with nucleic acid administration (i.e., antisense or locked nucleic acids). Nonetheless, as these small organic compounds have long half-lives, encapsulation drug delivery systems, such as liposomes or other biodegradable protective compositions, will lengthen these half-lives to a greater extent than either antibodies or nucleic acids. These small organic compounds described in this application are designed de novo to have desirable characteristics, such as for drug-like properties. Although it is not necessary to understand the mechanism of an invention, it is believed that these compounds are also structurally distinct from any previously described PCSK9 modulating small molecules and are reasonably expected to have different physicochemical properties from other PCSK9 binding compounds.

III. Clinical Therapeutics

In some embodiments, the present invention contemplates the administration of a small molecule PCSK9 allosteric inhibitor compound to a subject having a symptom of a cardiovascular disease. In one embodiment, the cardiovascular disease comprises hypercholesterolemia. In one embodiment, the cardiovascular disease comprises hypertension. In one embodiment, the hypercholesterolemia comprises elevated low density lipoprotein levels.

In some embodiments, the present invention contemplates the administration of a small molecule PCSK9 allosteric inhibitor compound to a subject having a symptom of a metabolic disease. In one embodiment, the metabolic disease comprises diabetes.

Although it is not necessary to understand the mechanism of an invention, it is believed that the administration of a PCSK9 allosteric inhibitor small molecule compound (i.e., such as those described herein) induces a conformational shift of the PCSK9 protein such that the affinity of the low density lipoprotein binding site for a low density lipoprotein receptor is decreased, wherein PCSK9/LDL-R complex formation is decreased. The decrease in PCSK9/LDL-R complex formation results in an increase in the bioavailability of LDL-R receptors for binding to circulating LDL, thereby increasing the internalization and clearance of LDL by LDL-R. It is further believed that a small molecule PCSK9 allosteric inhibitor compound may result in increased bioavailability of hepatocyte cell LDL-Rs.

Further, although it is not necessary to understand the mechanism of an invention, it is believed that the administration of a PCSK9 allosteric activator small molecule compound (i.e., such as those described herein) induces a conformational shift of the PCSK9 protein such that the affinity of the low density lipoprotein binding site for a low density lipoprotein receptor is increased, wherein PCSK9/LDL-R complex formation is increased or stabilized. The increase or stabilization in PCSK9/LDL-R complex formation results in a decrease in the bioavailability of LDL-R receptors for binding to circulating LDL, thereby decreasing the internalization and clearance of LDL by LDL-R. It is further believed that a PCSK9 allosteric activator compound may result in decreased bioavailability of hepatocyte cell LDL-Rs.

A. Hypercholesterolemia

Hypercholesterolemia (also spelled hypercholesterolaemia) is the presence of high levels of cholesterol in the blood. It is a form of "hyperlipidemia" (elevated levels of lipids in the blood) and "hyperlipoproteinemia" (elevated levels of lipoproteins in the blood). Durrington, P "Dyslipidaemia" *The Lancet* 362(9385):717-731. Hypercholesterolemia is typically due to a combination of environmental and genetic factors. Environmental factors include obesity and dietary choices. Genetic contributions are usually due to the additive effects of multiple genes, though occasionally may be due to a single gene defect such as in the case of familial hypercholesterolaemia. A number of secondary causes exist including: diabetes mellitus type 2, obesity, alcohol, monoclonal gammopathy, dialysis, nephrotic syndrome, obstructive jaundice, hypothyroidism, Cushing's syndrome, anorexia nervosa, medications (thiazide diuretics, ciclosporin, glucocorticoids, beta blockers, retinoic acid). Bhatnagar et al., (2008) "Hypercholesterolaemia and its management" *BMJ* 337: a993. Genetic abnormalities are in some cases completely responsible for hypercholesterolemia, such as in familial hypercholesterolemia where there is one or more genetic mutations in the autosomal dominant APOB gene, the autosomal recessive LDLRAP1 gene, autosomal dominant familial hypercholesterolemia (HCHOLA3) variant of the PCSK9 gene, or the LDL receptor gene. "Hypercholesterolemia" *Genetics Home Reference* U.S. National Institutes of Health, ghr.nlm.nih.gov/condition=hypercholesterolemia. Even when there is no single mutation responsible for hypercholesterolemia, genetic predisposition still plays a major role in combination with sedentary lifestyle, obesity, or an atherogenic diet. Citkowitz et al., (2010) "Polygenic Hypercholesterolemia". *eMedicine Medscape*, emedicine.medscape.com/article/121424-overview.

Cholesterol is a sterol. It is one of three major classes of lipids which all animal cells utilize to construct their membranes and is thus manufactured by all animal cells. Plant cells do not manufacture cholesterol. It is also the precursor of the steroid hormones, bile acids and vitamin D. Since cholesterol is insoluble in water, it is transported in the blood plasma within protein particles (lipoproteins). Lipoproteins are classified by their density: very low density lipoprotein (VLDL), intermediate density lipoprotein (IDL), low density lipoprotein (LDL) and high density lipoprotein (HDL). Biggerstaff et al., (2004). "Understanding lipoproteins as transporters of cholesterol and other lipids" *Adv Physiol Educ* 28 (1-4): 105-6. All the lipoproteins carry cholesterol, but elevated levels of the lipoproteins other than HDL (termed non-HDL cholesterol), particularly LDL-cholesterol are associated with an increased risk of atherosclerosis and coronary heart disease. Carmena et al., (2004) "Atherogenic lipoprotein particles in atherosclerosis" *Circulation* 109(23 Suppl 1): III 2-7. In contrast, higher levels of HDL cholesterol are protective. Kontush et al., (2006) "Antiatherogenic small, dense HDL-guardian angel of the arterial wall?" *Nat Clin Pract Cardiovasc Med* 3(3):144-153. Elevated levels of non-HDL cholesterol and LDL in the blood may be a consequence of diet, obesity, inherited (genetic) diseases (such as LDL receptor mutations in familial hypercholesterolemia), or the presence of other diseases such as diabetes and an underactive thyroid. Total cholesterol is the amount of all of the fats in your blood. These fats are called lipids. There are different types of lipid that make up your total cholesterol. The two most important types are: low density lipoprotein (LDL)—"bad" cholesterol and high density lipoprotein (HDL)—"good" cholesterol. High cholesterol, especially "bad" cholesterol (LDL), can clog your arteries. This may reduce blood flow to your heart. It can lead to heart disease, stroke, or heart attack. Cholesterol is measured in milligrams per deciliter (mg/dL). In conditions such as heart disease or diabetes, LDL cholesterol should stay below 100 mg/dL. If there is a risk for heart disease, LDL cholesterol should be lower than 130 mg/dL. In general, LDL cholesterol should be lower than 160-190 mg/dL. Alternative, HDL "good" cholesterol should be high. For example, HDL levels in men should be above 40 mg/dL, while HDL levels should be above 50 mg/dL for women.

One symptom of hypercholesterolemia comprises a long-standing elevation of serum cholesterol that can lead to atherosclerosis. Bhatnagar et al., (2008) "Hypercholesterolaemia and its management" *BMJ* 337: a993. Over a period of decades, chronically elevated serum cholesterol contributes to formation of atheromatous plaques in the arteries. This can lead to progressive stenosis (narrowing) or even complete occlusion (blockage) of the involved arteries. Alternatively smaller plaques may rupture and cause a clot to form and obstruct blood flow. Finn AV, Nakano M, Narula J, Kolodgie FD, Virmani R (July 2010). "Concept of vulnerable/unstable plaque" *Arterioscler. Thromb. Vasc. Biol.* 30(7): 1282-1292. A sudden occlusion of a coronary artery results in a myocardial infarction or heart attack. An occlusion of an artery supplying the brain can cause a stroke. If the development of the stenosis or occlusion is gradual blood supply to the tissues and organs slowly diminishes until organ function becomes impaired. At this point that tissue ischemia (restriction in blood supply) may manifest as specific symptoms including, but not limited to, temporary ischemia of the brain (commonly referred to as a transient ischemic attack) may manifest as temporary loss of vision, dizziness and impairment of balance, aphasia (difficulty speaking), paresis (weakness) and paresthesia (numbness or tingling), usually on one side of the body. Insufficient blood supply to the heart may manifest as chest pain, and ischemia of the eye may manifest as transient visual loss in one eye. Insufficient blood supply to the legs may manifest as calf pain when walking, while in the intestines it may present as abdominal pain after eating a meal. Grundy et al., (1998) "Primary prevention of coronary heart disease: guidance from Framingham: a statement for healthcare professionals from the AHA Task Force on Risk Reduction. American Heart Association" *Circulation* 97(18):1876-1887.

B. Hypocholesterolemia

Hypocholesterolemia is the presence of abnormally low (hypo-) levels of cholesterol in the blood (-emia). Although the presence of high total cholesterol (hyper-cholesterolemia) correlates with cardiovascular disease, a defect in the body's production of cholesterol can lead to adverse consequences as well. Cholesterol is an essential component of mammalian cell membranes and is required to establish proper membrane permeability and fluidity. It is not clear if a lower than average cholesterol level is directly harmful; it is often encountered in particular illnesses.

Possible causes of low cholesterol include, but are not limited to, statins, hyperthyroidism, or an overactive thyroid gland, adrenal insufficiency, liver disease, malabsorption (inadequate absorption of nutrients from the intestines), such as in celiac disease, malnutrition, abetalipoproteinemia (a genetic disease that causes cholesterol readings below 50 mg/dl), hypobetalipoproteinemia (a genetic disease that causes cholesterol readings below 50 mg/dl, manganese deficiency, Smith-Lemli-Opitz syndrome, Marfan syndrome, leukemias and other hematological diseases.

Demographic studies suggest that low cholesterol is associated with increased mortality, mainly due to depression, cancer, hemorrhagic stroke, aortic dissection and respiratory diseases. Jacobs et al., (1992). "Report of the Conference on Low Blood Cholesterol: Mortality Associations" *Circulation* 86 (3): 1046-1060; and Suarez E. C., (1999) "Relations of trait depression and anxiety to low lipid and lipoprotein concentrations in healthy young adult women". *Psychosom Med* 61(3): 273-279. It is also possible that whatever causes the low cholesterol level also causes mortality, and that the low cholesterol is simply a marker of poor health.

C. Diabetes

Diabetes affects more than 20 million Americans. Over 40 million Americans have pre-diabetes (which often develops before type 2 diabetes). Diabetes is usually a lifelong (chronic) disease in which there is a high level of sugar in the blood. Insulin is a hormone produced by the pancreas to control blood sugar. Diabetes can be caused by too little insulin, resistance to insulin, or both. To understand diabetes, it is important to first understand the normal process by which food is broken down and used by the body for energy.

Several things happen when food is digested. A sugar called glucose enters the bloodstream. Glucose is a source of fuel for the body. An organ called the pancreas makes insulin. The role of insulin is to move glucose from the bloodstream into muscle, fat, and liver cells, where it can be used as fuel.

People with diabetes have high blood sugar because their body cannot move sugar into fat, liver, and muscle cells to be stored for energy. This is because either their pancreas does not make enough insulin or their cells do not respond to insulin normally.

There are two major types of diabetes. The causes and risk factors are different for each type. Type 1 diabetes can occur at any age, but it is most often diagnosed in children, teens, or young adults. In this disease, the body makes little or no insulin. Daily injections of insulin are needed. The exact cause is unknown. Type 2 diabetes makes up most diabetes cases. It most often occurs in adulthood. But because of high obesity rates, teens and young adults are now being diagnosed with it. Many people with type 2 diabetes do not know they have it.

Gestational diabetes is high blood sugar that develops at any time during pregnancy in a woman who does not have diabetes.

Diabetes symptoms may result from high blood sugar level and include, but are not limited to, blurry vision, excess thirst, fatigue, hunger, urinating often and weight loss.

IV. Pharmaceutical Compositions

The present invention further provides pharmaceutical compositions (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, (e.g., intrathecal or intraventricular), administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral, sublingual or buccal administration include powders or granules, suspensions or solutions in water or non-aqueous media, capsules, gels, drops, strips, gums, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

In some embodiment, the pharmaceutical compositions may further comprise other drugs and/or hormones. For example, the pharmaceutical composition may further comprise a statin drug. Statins (or HMG-CoA reductase inhibitors) are a class of drugs used to lower cholesterol levels by inhibiting the enzyme HMG-CoA reductase, which plays a role in the production of cholesterol in the liver. Increased cholesterol levels have been associated with cardiovascular diseases, and statins are therefore used in the prevention of these diseases. Lewington et al., "Blood cholesterol and vascular mortality by age, sex, and blood pressure: a meta-analysis of individual data from 61 prospective studies with 55,000 vascular deaths" Lancet 370(9602): 1829-1839 (2007). Research has found that statins are most effective for treating cardiovascular disease (CVD) as a secondary prevention strategy, with questionable benefit in those with elevated cholesterol levels but without previous CVD. Taylor et al. "Statins for the primary prevention of cardiovascular disease". In: Taylor, Fiona. Cochrane Database Syst Rev (1) (2011). Statins have rare but severe adverse effects, particularly muscle damage.

Specific examples of statins include, but are not limited to, atorvastatin (Lipitor® and Torvast®), fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®) and simvastatin (Zocor®, Lipex®). Several combination preparations of a statin and another agent, such as ezetimibe/simvastatin, are also available.

Specific examples of cardiovascular drugs include, but are not limited to, propranolol, digitalis, amlodipine besylate, and nifedipine.

Specific examples of other pharmaceutical compositions may further include, but are not limited to, exetimibe (Zetia®), amlodipine besylate (Norvasc®), niacin, sitagliptin (Januvia®), metformin or orlistat (Alli®/Xenical®).

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active pharmaceutical ingredient(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on ECsos found to be effective in in vitro and in vivo animal models or based on the small molecule compounds described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the small molecule compound is administered in maintenance doses, ranging from 0.01 µg to 100 g per kg of body weight, once or more daily, to once every 20 years.

In one embodiment, the present invention further contemplates a commercial package comprising (a) a pharmaceutical composition comprising a small molecule compound as contemplated herein; and (b) instructions for the use thereof for treatment of hypercholesterolemia. In one embodiment, the present invention further contemplates a commercial package comprising (a) a pharmaceutical composition comprising a small molecule compound as contemplated herein; and (b) instructions for the use thereof for treatment of hypocholesterolemia. In one embodiment, the present invention further contemplates a commercial package comprising (a) a pharmaceutical composition comprising a small molecule compound as contemplated herein; and (b) instructions for the use thereof for inhibition of PCSK9 protein biological activity. In one embodiment, the present invention further contemplates a commercial package comprising (a) a pharmaceutical composition comprising a small molecule compound as contemplated herein; and (b) instructions for the use thereof for increasing the biological activity of PCSK9 protein. In one embodiment, the present invention further contemplates a commercial package as a kit.

In one embodiment, the present invention further contemplates a kit comprising (a) a pharmaceutical composition comprising a small molecule compound as contemplated herein; and (b) instructions for the use thereof for treatment of hypercholesterolemia. In one embodiment, the present invention further contemplates a kit comprising (a) a pharmaceutical composition comprising a small molecule compound as contemplated herein; and (b) instructions for the use thereof for treatment of hypocholesterolemia. In one embodiment, the present invention further contemplates a kit comprising (a) a pharmaceutical composition comprising a small molecule compound as contemplated herein; and (b) instructions for the use thereof for inhibition of PCSK9 protein biological activity. In one embodiment, the present invention further contemplates a kit comprising (a) a pharmaceutical composition comprising a small molecule compound as contemplated herein; and (b) instructions for the use thereof for increasing the biological activity of PCSK9 protein.

V. Description of Chemistry

Phenylpiperazine Scaffold—Synthesis:

The sulfonamido compounds of a phenylpiperazine scaffold of Formula I could be prepared using standard synthetic methods (Scheme 1):

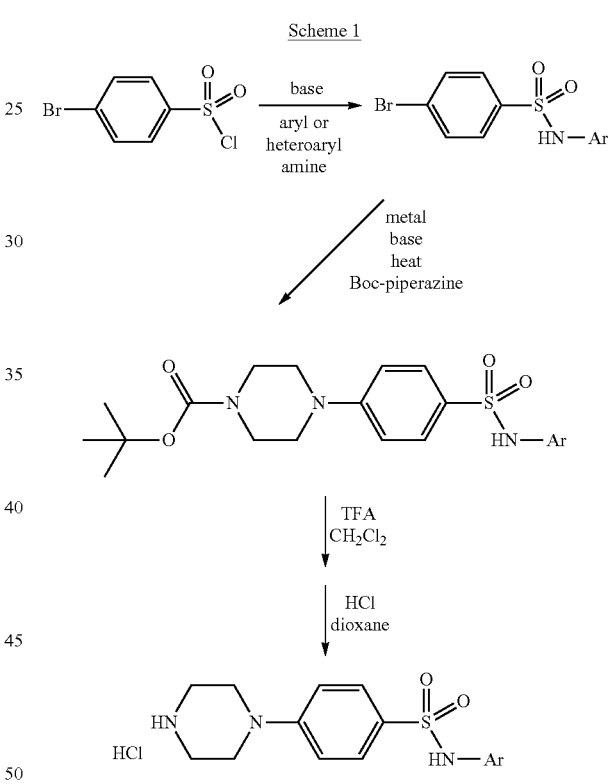

Related analogs are accessible by a variety of known procedures (Scheme 2).

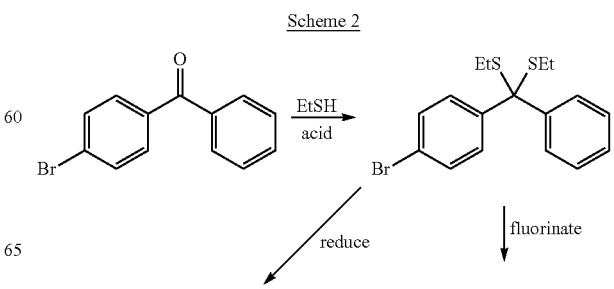

31
-continued
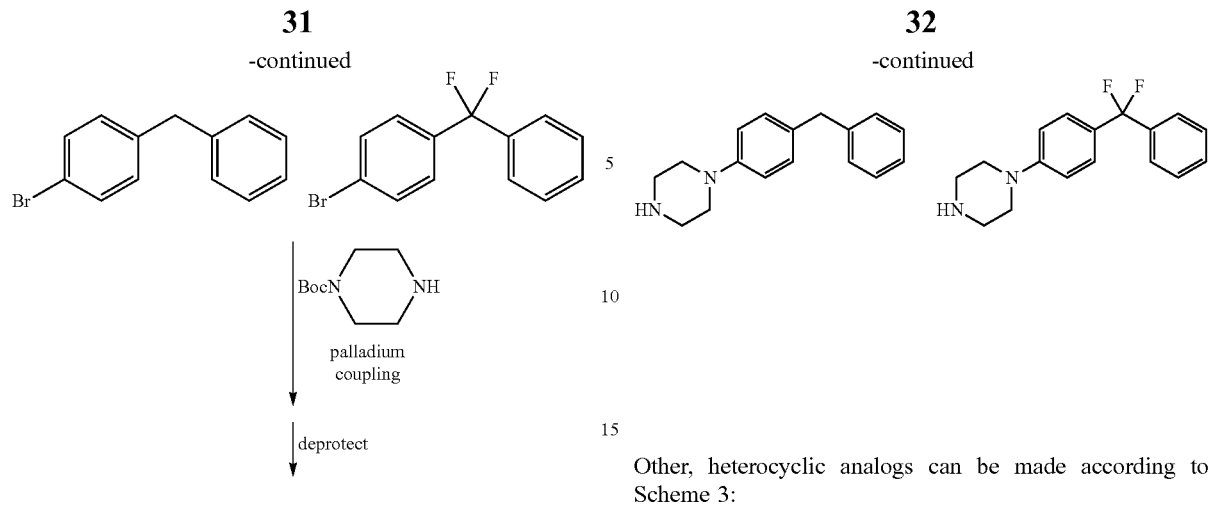
32
-continued
Other, heterocyclic analogs can be made according to Scheme 3:
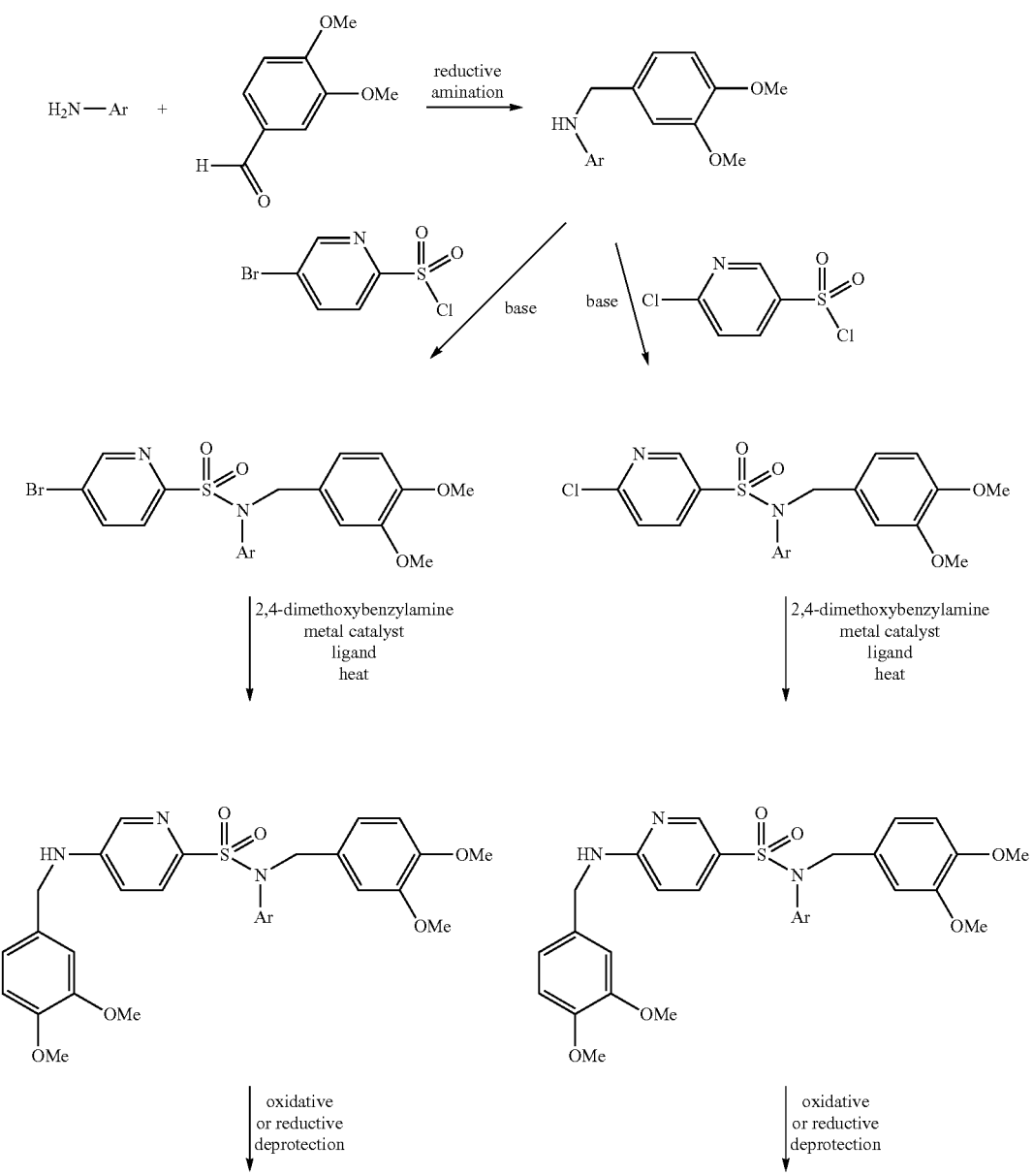

33 34

-continued

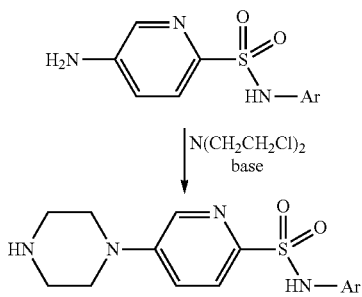
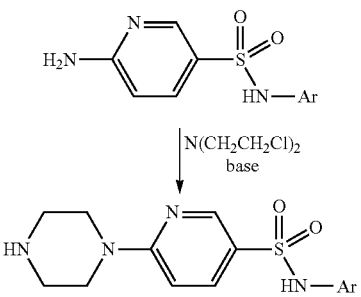

Piperidine analogs may be obtained by chemistry such as indicated in Scheme 4:

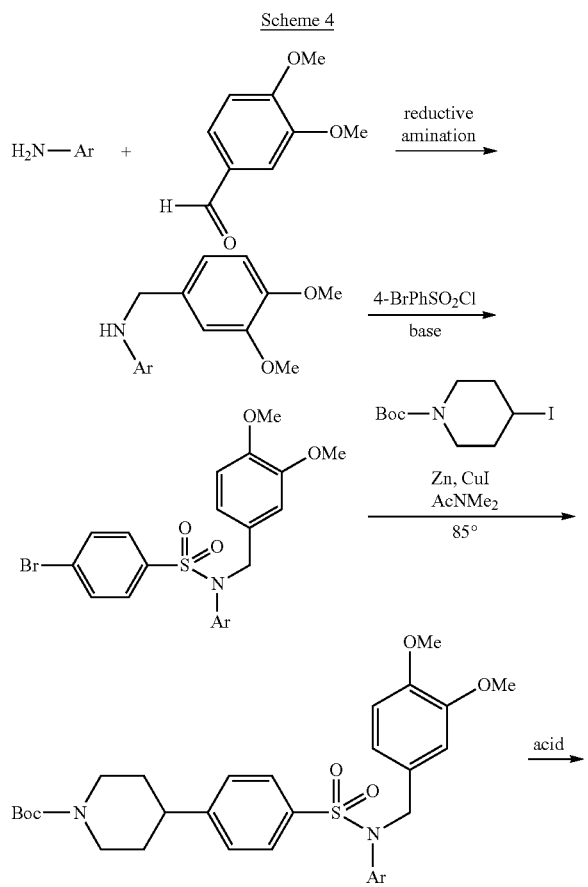

Tang, H. et al Bioorg. & Med. Chem Lett. 2010, 20, 6088-92

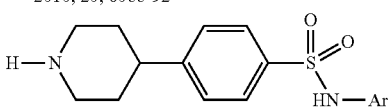

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Compound Synthesis

Compound 10

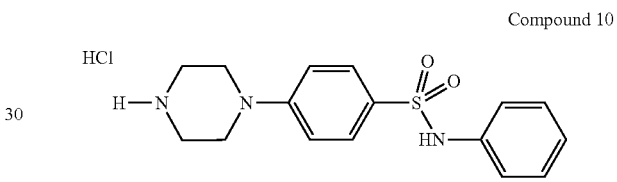

Step 1: Synthesis of 4-bromo-N-phenylbenzenesulfonamide
4-Bromobenzenesulfonyl chloride (2.00 g, 7.82 mmol, 1.0 eq), aniline (0.87 g, 9.34 mmol, 1.2 eq) and pyridine (3.00 g, 39.06 mmol, 5.0 eq) were dissolved in dichloromethane (25 mL) under nitrogen atmosphere and the solution was stirred at ambient temperature for 6 h. After complete consumption of starting material, the reaction mixture was diluted with dichloromethane and washed with 0.5 N aq HCl followed by water, saturated aq $NaHCO_3$ and brine. The organic extract was then dried over anhydrous sodium sulfate, filtered, and solvent evaporated from the filtrated under reduced pressure to afford 4-bromo-N-phenylbenzenesulfonamide as yellow solid (1.4 g, 57.3%). LCMS: Purity 99.69%. MS calculated for [M] 310.96 and found $[M-H]^+$ 309.88.

Step 2: Synthesis of tert-butyl 4-(4-(N-phenylsulfamoyl)phenyl)piperazine-1-carboxylate
A mixture of 4-bromo-N-phenylbenzenesulfonamide (1.00 g, 3.20 mmol, 1.0 eq), tert-butyl piperazine-1-carboxylate (0.71 g, 3.81 mmol, 1.2 eq), $K_2CO_3$ (0.89 g, 6.40 mmol, 2.0 eq), CuI (0.12 g, 0.640 mmol, 0.2 eq) and L-proline (0.11 g, 0.955 mmol, 0.3 eq) in DMSO (15 mL) was stirred at 90° C. for 18 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous $Na_2SO_4$, filtered and solvents evaporated from the filtrate under reduced pressure to obtain a crude, which was purified by flash chromatography on silica gel, 230-400 mesh, using gradient of ethyl acetate in hexanes as eluent to obtain tert-butyl 4-(4-(N-phenylsulfamoyl)phenyl)piperazine-1-carboxylate as yellow solid, yield (0.25 g, 18.7%). LCMS: Purity 84.26%. MS calculated for [M] 417.17 and found [M−H]+ 416.08.

Step 3: Synthesis of N-phenyl-4-(piperazin-1-yl)benzenesulfonamide

Trifluoroacetic acid (0.314 g, 2.75 mmol, 5.0 eq) was added to a solution of tert-butyl 4-(4-(N-phenylsulfamoyl)phenyl)piperazine-1-carboxylate (0.23 g, 0.55 mmol, 1.0 eq) in dichloromethane (10 mL) at ambient temperature and the mixture was stirred for 3 h. After complete consumption of starting material, solvents evaporated from the mixture under reduced pressure, the residue was diluted with aq. sodium bicarbonate and extracted with a mixture of methanol and dichloromethane (1:20). The combined organic extract was washed with brine, dried over anhydrous $Na_2SO_4$, filtered and solvents evaporated from the filtrate under reduced pressure to obtain N-phenyl-4-(piperazin-1-yl)benzenesulfonamide as off white solid (0.078 g, 93%). LCMS: Purity 98.69%. MS calculated for [M] 317.12 and found [M+H]+ 318.05.

Step 4: Synthesis of N-phenyl-4-(piperazin-1-yl)benzenesulfonamide Hydrochloride 4M HCl in 1,4-dioxane (2.0 mL) was added to a solution of N-phenyl-4-(piperazin-1-yl) benzene sulfonamide (0.03 g, 0.094 mmol, 1.0 eq) in dichloromethane (10 mL) at ambient temperature and the mixture was stirred 2 h. The solvent was evaporated under reduced pressure, the residue was triturated with diethyl ether, filtered and dried under vacuum to afford N-phenyl-4-(piperazin-1-yl) benzene sulfonamide hydrochloride as off white solid (0.022 g, 61%). LCMS: Purity 98.78%. MS calculated for [M] 317.12 and found [M+H]+ 318.41. $^1$H NMR (400 MHz, DMSO-d$_6$) δ: 10.07 (s, 1H), 9.07 (s, 2H), 7.58 (d, J=9.0 Hz, 2H), 7.21 (t, J=8.2 Hz, 2H), 7.08 (d, J=7.6 Hz, 2H), 7.03 (d, J=9.1 Hz, 2H), 6.99 (t, J=7.4 Hz, 1H), 3.50 (t, J=4.8 Hz, 4H), 3.17 (bs, 4H).

Compound 12

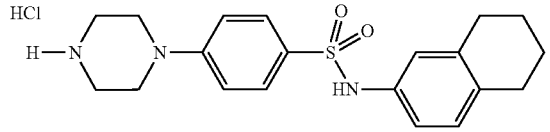

Step 1: Synthesis of 4-bromo-N-(5,6,7,8-tetrahydronaphthalen-2-yl)benzenesulfonamide.

4-Bromobenzenesulfonyl chloride (3.00 g, 11.70 mmol, 1.0 eq), 5,6,7,8-tetrahydronaphthalen-2-amine (2.07 g, 14.08 mmol, 1.2 eq) and pyridine (3.00 g, 39.06 mmol, 5.0 eq) were dissolved in dichloromethane (30 mL) under nitrogen atmosphere and the solution was stirred at ambient temperature for 3 h. After complete consumption of starting material, the reaction mixture was diluted with dichloromethane and washed with 0.5 N aq HCl followed by water, saturated aq NaHCO$_3$ and brine. The organic extract was then dried over anhydrous sodium sulfate, filtered, and solvent evaporated from the filtrated under reduced pressure to 4-bromo-N-(5,6,7,8-tetrahydronaphthalen-2-yl) benzene sulfonamide as yellow sticky mass (2.2 g, 51.1%). LCMS: Purity 81.44%. MS calculated for [M] 365.01 and found [M−H]+ 363.92.

Step 2: Synthesis of tert-butyl 4-(4-(N-(5,6,7,8-tetrahydronaphthalen-2-yl)sulfamoyl)phenyl)piperazine-1-carboxylate A mixture of 4-bromo-N-(5,6,7,8-tetrahydronaphthalen-2-yl) benzene sulfonamide (2.00 g, 5.47 mmol, 1.0 eq), tert-butyl piperazine-1-carboxylate (1.2 g, 6.57 mmol, 1.2 eq), $K_2CO_3$ (3.48 g, 16.39 mmol, 3.0 eq), Pd$_2$(dba)$_3$ (0.23 g, 0.22 mmol, 0.04 eq) and rec-BINAP (0.48 g, 0.77 mmol, 0.14 eq) in 1,4-Dioxane (25.0 mL) was stirred at 100° C. for 18 h. After complete consumption of starting material, the mixture was cooled to ambient temperature and partitioned between water and ethyl acetate. The organic extract was separated and the aqueous extract was again extracted with ethyl acetate. The combined organic extract was washed with brine, dried over anhydrous $Na_2SO_4$, filtered and solvents evaporated from the filtrate under reduced pressure to obtain a crude, which was purified by flash chromatography on silica gel, 230-400 mesh, using gradient of ethyl acetate in hexanes as eluent to obtain tert-butyl 4-(4-(N-(5,6,7,8-tetrahydronaphthalen-2-yl)sulfamoyl)phenyl)piperazine-1-carboxylate as yellow solid (0.35 g, 14%). LCMS: Purity 80.35%. MS calculated for [M] 471.22 and found [M+H]+ 472.29.

Step 3: Synthesis of 4-(piperazin-1-yl)-N-(5,6,7,8-tetrahydronaphthalen-2-yl)benzenesulfonamide Trifluoroacetic acid (0.36 g, 3.18 mmol, 5.0 eq) was added to a solution of tert-butyl 4-(4-(N-(5,6,7,8-tetrahydronaphthalen-2-yl)sulfamoyl)phenyl)piperazine-1-carboxylate (0.30 g, 0.64 mmol, 1.0 eq) in dichloroemthane (10 mL) at ambient temperature and the mixture was stirred for 2 h. After complete consumption of starting material, solvents evaporated from the mixture under reduced pressure, the residue was diluted with aq. sodium bicarbonate and extracted with dichloromethane. The combined organic extract was washed with brine, dried over anhydrous $Na_2SO_4$, filtered and solvents evaporated from the filtrate under reduced pressure to obtain 4-(piperazin-1-yl)-N-(5,6,7,8-tetrahydronaphthalen-2-yl)benzenesulfonamide as off white solid (0.052 g, 21.1%). LCMS: Purity 98.23%. MS calculated for [M] 371.17 and found [M+H]+ 371.10.

Step 4: Synthesis of 4-(piperazin-1-yl)-N-(5,6,7,8-tetrahydronaphthalen-2-yl)benzenesulfonamide Hydrochloride 4M HCl in 1,4-dioxane (2.5 mL) was added to a solution of 4-(piperazin-1-yl)-N-(5,6,7,8-tetrahydronaphthalen-2-yl) benzenesulfonamide (0.05 g, 0.13 mmol, 1.0 eq) in dichloromethane (10 mL) at ambient temperature and the mixture was stirred 2 h. The solvent was evaporated under reduced pressure, the residue was triturated with diethyl ether, filtered and dried under vacuum to afford 4-(piperazin-1-yl)-N-(5,6,7,8-tetrahydronaphthalen-2-yl)benzenesulfonamide hydrochloride as off white solid (0.022 g, 61%). LCMS: Purity 99.59%. MS calculated for [M] 371.17 and found [M+H]+ 372.49. $^1$H NMR (400 MHz, DMSO-d$_6$) δ: 9.85 (s, 1H), 9.06 (s, 2H), 7.58 (d, J=9.0 Hz, 2H), 7.04 (d, J=9.0 Hz, 2H), 6.86 (d, J=8.2 Hz, 1H), 6.80 (d, J=6.1 Hz & 2.1 Hz, 1H), 6.76 (d, J=1.8 Hz, 1H), 3.50 (t, J=4.8 Hz, 4H), 3.17 (t, J=4.8 Hz, 4H), 2.57 (bs, 4H), 1.65 (bs, 4H).

Compound 14

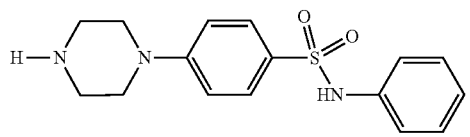

Preparation of N-phenyl-4-(piperidin-4-yl)benzenesulfonamide

The title compound was prepared by a method similar to Scheme 4. MS calculated for [M] 316.12 and found [M+H]+ 317.16.

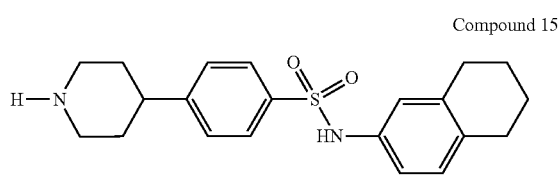 [SMILES: O=S(=O)(Nc1ccc2c(c1)CCCC2)c1ccc(C2CCNCC2)cc1]

Compound 15

Preparation of 4-(piperidin-4-yl)-N-(5,6,7,8-tetrahydronaphthalen-2-yl)benzenesulfonamide The title compound was prepared by a method similar to Scheme 4. MS calculated for [M] 370.17 and found [M+H]$^+$ 371.23.

Biological Assays

The compounds of the present disclosure may be tested for binding to, inhibition of, and/or modulation of PCSK9 activity according to the following protocols.

Cell Culture

Cells, such as HepG2, HuH7, FL83B, or a cell line transfected with a short-hairpin PCSK9 knockdown sequence (e.g., HepG2/shPCSK9, HuH7/shPCSK9) can be cultured following routine procedures, such as those described by Benjannet et al., "Effects of the prosegment and pH on the activity of PCSK9: evidence for additional processing events" *J Biol Chem.* 285(52): 40965-40978 (2010), which is hereby incorporated by reference in its entirety.

LDLR Flow Cytometric Analysis

LDLR levels can be measured using flow cytometry or fluorescence activated cell sorting (FACS) using protocols adapted from Benjannet et al., "Effects of the prosegment and pH on the activity of PCSK9: evidence for additional processing events" *J Biol Chem.* 285(52): 40965-40978 (2010) and "Composition and Methods of Use of Small Molecules as Binding Ligands for the Modulation of Proprotein Convertase Subtilisin/Kexin Type 9 (PCSK9) Protein Activity" (WO2016029037), which are incorporated by reference in their entirety.

Cells, such as HepG2, HuH7, FL83B, or a cell line transfected with a short-hairpin PCSK9 knockdown sequence such as HepG2/shPCSK9, HuH7/shPCSK9, or FL83B/shPCSK9 are plated and cultured at 37° C. for 12-24 h. Culture media is removed and replaced with fresh culture media or culture media plus a predetermined amount of recombinant PCSK9, for example a 10 nM final concentration of PCSK9. Cell culture media can be composed of DMEM (Invitrogen) with 10% fetal bovine serum (Life Technologies) supplemented with penicillin-streptomycin (Life Technologies). Cells are dosed with small molecule test compounds at doses ranging from 0 nM to 100 uM Following an incubation period of specified length, such as 6 hours, the media is removed and the cells are rinsed three times with a rinse solution (i.e., Dulbecco's phosphate buffered saline (D-PBS, Life Technologies) supplemented with 0.5% bovine serum albumin (BSA, Sigma) and 1 g/L glucose (Sigma)). The fluid is then removed, and cells are released from the plate using TrypLE Express (Life Technologies) per manufacturer's recommend procedures, such as incubation for 5-10 minutes at 37° C. The TyrpLE-Cell suspension is then transferred to 15 mL conical tubes, volume is increased to 2 mL with D-PBS supplemented with 0.5% BSA and 1 g/mL glucose, and the tubes are centrifuged at 250× gravity for 10 minutes. Following centrifugation, the supernatant is aspirated and the cell pellet is resuspended in 100 uL D-PBS containing 0.5% BSA and 1 g/mL glucose, and cells are labeled with anti-LDLR antibody per the manufacturer's recommended procedure. The cells are then pelleted by centrifugation, resuspended in 300 uL PBS and counterstained with 4',6-Diamidino-2-phenylindole (DAPI, Cayman Chemical) as a cell viability marker, other cell viability markers such as 7-aminoactinomycin D (7AAD, Life Technologies) have also been described in the art.

Cells are analyzed for both cell viability marker (dead cells) and LDLR in live cells using a flow cytometer per the manufacturer's operating manual. Cells incubated with small molecule compounds that are inhibitors of PCSK9 will be expected to show increased amounts of LDLR, relative to control (no compound) specimens, and cells incubated with small molecule compounds that are activators of PCSK9 will be expected to show decreased amounts of LDLR relative to control (no compound) specimens.

Cellular DiI-LDL Uptake Analysis

Cellular DiI-LDL uptake can be measured using protocols adapted from Benjannet et al., "Effects of the prosegment and pH on the activity of PCSK9: evidence for additional processing events" *J Biol Chem.* 285(52): 40965-40978 (2010) and "Composition and Methods of Use of Small Molecules as Binding Ligands for the Modulation of Proprotein Convertase Subtilisin/Kexin Type 9 (PCSK9) Protein Activity" (WO2016029037), which are incorporated by reference in their entirety.

Cells, such as HepG2, HuH7, FL83B, or a cell line transfected with a short-hairpin PCSK9 knockdown sequence such as HepG2/shPCSK9, HuH7/shPCSK9, or FL83B/shPCSK9 are plated and cultured at 37° C. for 12-24 h. Culture media is removed and replaced with fresh lipoprotein-depleted culture media supplemented with 5 ug/mL of DiI-LDL (Kalen Biomedical) or lipoprotein-depleted culture media supplemented with 5 ug/mL of DiI-LDL plus a predetermined concentration of recombinant PCSK9, for example a 10 nM final concentration of PCSK9. Lipoprotein-depleted culture media can be composed of DMEM (Invitrogen) with 10% lipoprotein-depleted fetal bovine serum (Kalen Biomedical) and supplemented with penicillin-streptomycin (Life Technologies). Cells are dosed with small molecule test compounds at doses ranging from 0 nM to 100 uM.

Following an incubation period of specified length, such as 6 hours, Hoechst 33342 (AnaSpec) stain is added to the cell media per manufacturer's instructions and incubated for a specified length (e.g., 30 minutes). The lipoprotein-depleted media is removed and cells rinsed three times with phosphate buffered saline. A final volume of phosphate buffered saline is added back to the wells. The DiI fluorescence is measured with a plate reader using an exciting wavelength of 550 nm and the resulting emission at 590 nm is measured. The Hoechst stain fluorescence is measured with a plate reader using an exciting wavelength of 355 nm and the resulting emission at 460 nm is measured.

Cells are analyzed by for both Hoechst stain (DNA content) and DiI-LDL fluorescence. Cells incubated with small molecule compounds that are inhibitors of PCSK9 will be expected to show increased amounts of DiI-LDL fluorescence, relative to control (no compound) specimens, and cells incubated with small molecule compounds that are activators of PCSK9 will be expected to show decreased amounts of DiI-LDL fluorescence relative to control (no compound) specimens.

LDL Uptake Cell-Based Assay Kit

LDL uptake and LDLR expression can also be measured in cells, such as HepG2 or HuH7 cells, using a commercial kit (Cayman Chemical Co., Catalog #10011125) and the accompanying protocols provided by the manufacturer.

Back-Scattering Interferometry Direct Binding Measurement

Direct binding can be measured using Back-Scattering Interferometry (BSI), which has been previously described in "Interferometric detection system and method" (EP 1210581), "Free solution measurement of molecular interactions by backscattering interferometry" (WO 2009039466), "Temperature-stable interferometer" (WO 2009076372), and "Improved event detection for backscattering interferometry" (WO 2013158300); each of which are hereby incorporated by reference in their entirety.

Representative Table of Cell Activity of PCSK9 Modulating Compounds

TABLE 1

Representative Cell Activity of PCSK9 Inhibitory Compounds

| Compound # | Structure | IUPAC Chemical Name | Uptake Assay: % Inhibition of 2.5 ug/mL recombinant PCSK9 @ X compound dose | LDLR Flow Assay: % Inhibition of 5.0 ug/mL recombinant PCSK9 @ X compound dose |
|---|---|---|---|---|
| Compound 1 | 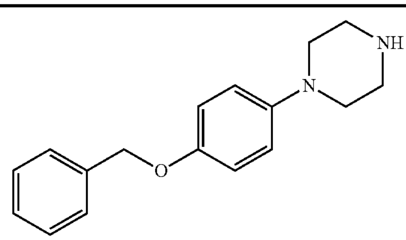 | 1-(4-(benzyloxy)phenyl)piperazine | >100% @ 10 uM | ~16% @ 1.25 uM, ~34% @ 10 uM |
| Compound 2 | 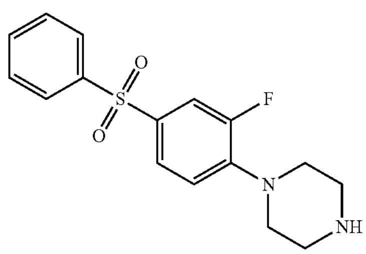 [SMILES: O=S(=O)(c1ccccc1)c1ccc(N2CCNCC2)c(F)c1] | 1-(2-fluoro-4-(phenylsulfonyl)phenyl)piperazine | >100% @ 20 uM | ~45% @ 1.25 uM, ~66% @ 5 uM |
| Compound 3 | 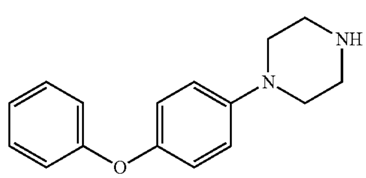 [SMILES: c1ccc(Oc2ccc(N3CCNCC3)cc2)cc1] | 1-(4-phenoxyphenyl)piperazine | >100% @ 10 uM | ~20% @ 1.25 uM, ~30% @ 10 uM |
| Compound 4 | 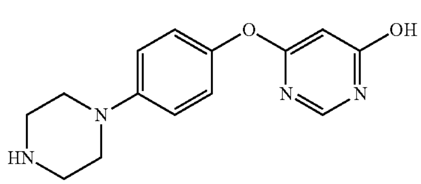 [SMILES: Oc1cc(Oc2ccc(N3CCNCC3)cc2)ncn1] | 6-(4-(piperazin-1-yl)phenoxy)pyrimidin-4-ol | | ~19% @ 0.313 uM, ~30% @ 1.25 uM |
| Compound 5 | 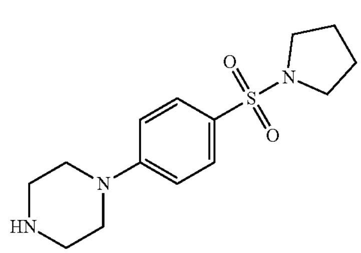 [SMILES: O=S(=O)(c1ccc(N2CCNCC2)cc1)N1CCCC1] | 1-(4-(pyrrolidin-1-ylsulfonyl)phenyl)piperazine | | ~10% @ 1.25 uM, ~20% @ 10 uM |

TABLE 1-continued

Representative Cell Activity of PCSK9 Inhibitory Compounds

| Compound # | Structure | IUPAC Chemical Name | Uptake Assay: % Inhibition of 2.5 ug/mL recombinant PCSK9 @ X compound dose | LDLR Flow Assay: % Inhibition of 5.0 ug/mL recombinant PCSK9 @ X compound dose |
|---|---|---|---|---|
| Compound 6 | 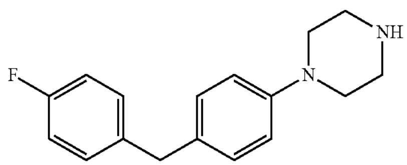 [SMILES: Fc1ccc(Cc2ccc(N3CCNCC3)cc2)cc1] | 1-(4-(4-fluorobenzyl)phenyl)piperazine | >100% @ 5 uM | ~15% @ 1.25 uM, ~40% @ 10 uM |
| Compound 7 | 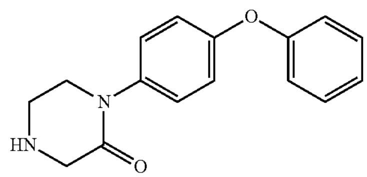 [SMILES: O=C1CNCCN1c1ccc(Oc2ccccc2)cc1] | 1-(4-phenoxyphenyl)piperazin-2-one | | ~18% @ 1.25 uM |
| Compound 8 | 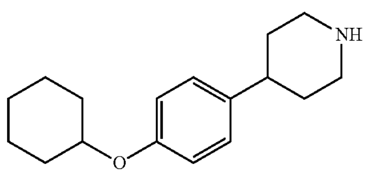 [SMILES: c1cc(C2CCNCC2)ccc1OC1CCCCC1] | 4-(4-(cyclohexyloxy)phenyl)piperidine | >100% @ 5 uM | ~15% @ 0.313 uM, ~25% @ 1.25 uM ~35% @ 10 uM |
| Compound 9 | 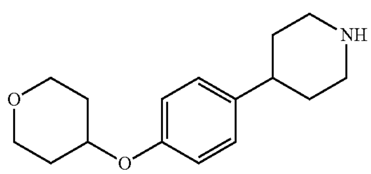 [SMILES: c1cc(C2CCNCC2)ccc1OC1CCOCC1] | 4-(4-((tetrahydro-2H-pyran-4-yl)oxy)phenyl)piperidine | | ~23% @ 20 uM |
| Compound 10 | 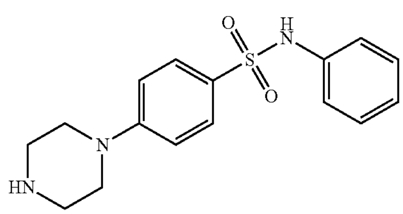 [SMILES: O=S(=O)(Nc1ccccc1)c1ccc(N2CCNCC2)cc1] | N-phenyl-4-(piperazin-1-yl)benzenesulfonamide | >100% @ 20 uM | >10% @ 1.25 uM, >25% @ 10 uM, >40% @ 20 uM |
| Compound 11 | 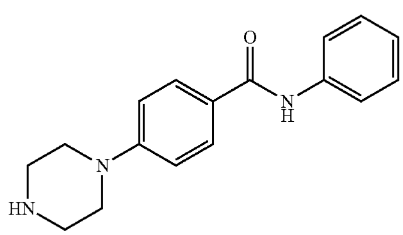 [SMILES: O=C(Nc1ccccc1)c1ccc(N2CCNCC2)cc1] | N-phenyl-4-(piperazin-1-yl)benzamide | ~49% @ 20 uM | |
| Compound 12 | 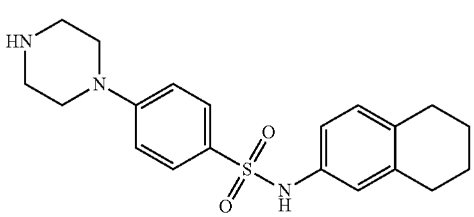 [SMILES: O=S(=O)(Nc1ccc2c(c1)CCCC2)c1ccc(N2CCNCC2)cc1] | 4-(piperazin-1-yl)-N-(5,6,7,8-tetrahydronaphthalen-2-yl)benzenesulfonamide | ~66% @ 1.25 uM, >100% @ 2.5 uM | ~10% @ 1.25 uM, ~25% @ 10 uM, ~45% @ 20 uM |

TABLE 1-continued

Representative Cell Activity of PCSK9 Inhibitory Compounds

| Compound # | Structure | IUPAC Chemical Name | Uptake Assay: % Inhibition of 2.5 ug/mL recombinant PCSK9 @ X compound dose | LDLR Flow Assay: % Inhibition of 5.0 ug/mL recombinant PCSK9 @ X compound dose |
| --- | --- | --- | --- | --- |
| Compound 13 | 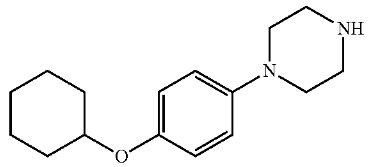 [SMILES: c1cc(N2CCNCC2)ccc1OC1CCCCC1] | 1-(4-(cyclohexyloxy)phenyl)piperazine | >100% @ 20 uM | ~20% @ 0.625 uM, ~40% @ 10 uM |
| Compound 14 | 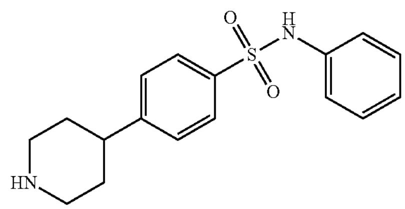 [SMILES: O=S(=O)(Nc1ccccc1)c1ccc(C2CCNCC2)cc1] | N-phenyl-4-(piperidin-4-yl)benzenesulfonamide | >100% @ 20 uM | |
| Compound 15 | 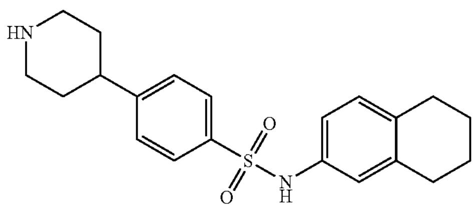 [SMILES: O=S(=O)(Nc1ccc2c(c1)CCCC2)c1ccc(C2CCNCC2)cc1] | 4-(piperidin-4-yl)-N-(5,6,7,8-tetrahydronaphthalen-2-yl)benzenesulfonamide | >50% @ 1.25 uM, >100% @ 2.5 uM | |

Unless otherwise defined, all technical and scientific terms used herein have the same meaning as commonly understood by one of ordinary skill in the art to which this disclosure pertains.

The disclosed embodiments illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims.

Thus, it should be understood that although the present disclosure has been specifically disclosed by exemplary embodiments and optional features, modification, improvement and variation of the disclosed embodiments may be implemented by those skilled in the art, and that such modifications, improvements and variations are considered to be within the scope of the present disclosure and claims. The materials, methods, and examples provided here are representative of preferred embodiments, are exemplary, and are not intended as limitations on the scope of the disclosure nor as limitations on the scope of the appended claims.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

We claim:

1. A method of modulating low density lipoprotein receptor internalization in a plurality of hepatocyte cells, comprising:
    inducing a conformational shift in
        a PCSK9 protein, wherein said protein comprises a low density lipoprotein receptor binding site, by binding a compound of Formula I:

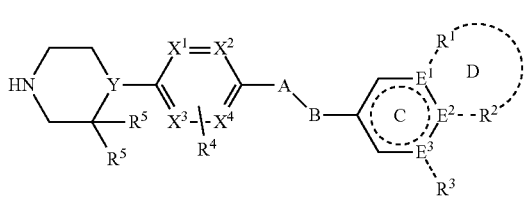

wherein
A is —O— or —CH$_2$—;
B is —CH$_2$— or absent;
Ring C is a 5 or 6 membered heteroaryl or heterocyclic ring, or a 6 membered aryl ring;
E$^1$, E$^2$, and E$^3$ are independently selected from C, CH, and N, wherein one of E$^1$, E$^2$, and E$^3$ may be absent;
R$^1$ and R$^2$ are independently selected from the group consisting of H, lower alkyl, hydroxy, amino, aminoalkyl, hydroxyalkyl, haloalkyl, carboxy, —CONH$_2$, —CONH-alkyl, nitrile, —S-alkyl, —O-alkyl, acyl, and oxo; or R$^1$ and R$^2$ with the atoms attached thereto combine to form a 5-6 membered fused aryl, heteroaryl, carbocyclic or heterocyclic ring D containing 0-3 heteroatoms, where Ring D may further be substituted at a position two atoms away from the juncture with Ring C;
R$^3$ is selected from the group consisting of H, lower alkyl, hydroxy, amino, aminoalkyl, hydroxyalkyl, haloalkyl, carboxy, —CONH$_2$, —CONH-alkyl, nitrile, —S-alkyl, —O-alkyl, acyl, and oxo;
R$^4$ is selected from the group consisting of H, OH, halogen, and lower alkyl;
each R$^5$ is hydrogen or both R$^5$ taken together are oxo;
Y is selected from the group consisting of N and CH; and
X$^1$, X$^2$, X$^3$, and X$^4$ are independently selected from the group consisting of CH, C—R$^4$, and N; or a pharmaceutically acceptable salt, hydrate, or solvate thereof,
to a binding site that induces allosteric modulation in the PCSK9 protein; wherein the plurality of hepatocyte cells comprise low density lipoproteins
whereby the rate of low density lipoprotein receptor internalization by said plurality of hepatocytes is modulated by said conformational shift.

2. The method of claim 1, whereby the rate of low density lipoprotein receptor internalization is increased.

3. The method of claim 1, whereby the rate of low density lipoprotein internalization is increased.

4. The method of claim 1, wherein the compound is formulated as a pharmaceutical composition comprising a pharmaceutically acceptable carrier or excipient.

5. The method of claim 4, wherein said pharmaceutical composition further comprises a second pharmaceutical drug compound.

6. The method of claim 5, wherein said second pharmaceutical drug compound is selected from the group consisting of a statin, a cardiovascular drug, a metabolic drug, and an antihypertensive drug.

7. The method of claim 1, where the compound is selected from:
1-(4-benzylphenyl)piperazine;
1-(4-(benzyloxy)phenyl)piperazine;
1-(4-phenoxyphenyl)piperazine;
1-(4-(4-(methylthio)phenoxy)phenyl)piperazine;
4-(4-(piperazin-1-yl)phenoxy)benzoic acid;
4-(4-(piperazin-1-yl)phenoxy)benzamide;
5-(4-(piperazin-1-yl)phenoxy)picolinamide;
1-(4-(3,4-dimethylphenoxy)phenyl)piperazine;
4-(4-phenoxyphenyl)piperidine;
4-(4-((tetrahydro-2H-pyran-4-yl)oxy)phenyl)piperidine;
4-(4-(piperidin-4-yl)phenoxy)piperidine;
1-(4-((tetrahydro-2H-pyran-4-yl)oxy)phenyl)piperazine;
1-(4-(piperidin-4-yloxy)phenyl)piperazine; and
1-(4-phenoxyphenyl)piperazin-2-one;
or a pharmaceutically acceptable salt thereof.

8. A method of modulating a population of low density lipoprotein receptors in a plurality of hepatocyte cells, comprising:
inducing a conformational shift in
a PCSK9 protein, wherein said protein comprises a low density lipoprotein receptor binding site,
by binding a compound of Formula I:

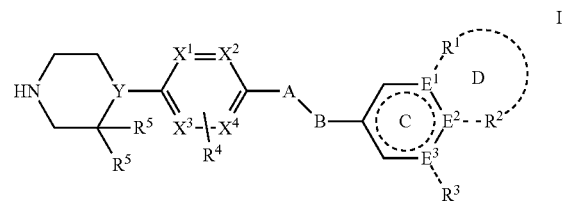

wherein
A is —O— or —CH$_2$—;
B is —CH$_2$— or absent;
Ring C is a 5 or 6 membered heteroaryl or heterocyclic ring, or a 6 membered aryl ring;
E$^1$, E$^2$, and E$^3$ are independently selected from C, CH, and N, wherein one of E$^1$, E$^2$, and E$^3$ may be absent;
R$^1$ and R$^2$ are independently selected from the group consisting of H, lower alkyl, hydroxy, amino, aminoalkyl, hydroxyalkyl, haloalkyl, carboxy, —CONH$_2$, —CONH-alkyl, nitrile, —S-alkyl, —O-alkyl, acyl, and oxo; or R$^1$ and R$^2$ with the atoms attached thereto combine to form a 5-6 membered fused aryl, heteroaryl, carbocyclic or heterocyclic ring D containing 0-3 heteroatoms, where Ring D may further be substituted at a position two atoms away from the juncture with Ring C;
R$^3$ is selected from the group consisting of H, lower alkyl, hydroxy, amino, aminoalkyl, hydroxyalkyl, haloalkyl, carboxy, —CONH$_2$, —CONH-alkyl, nitrile, —S-alkyl, —O-alkyl, acyl, and oxo;
R$^4$ is selected from the group consisting of H, OH, halogen, and lower alkyl;
each R$^5$ is hydrogen or both R$^5$ taken together are oxo;
Y is selected from the group consisting of N and CH; and
X$^1$, X$^2$, X$^3$, and X$^4$ are independently selected from the group consisting of CH, C—R$^4$, and N; or a pharmaceutically acceptable salt, hydrate, or solvate thereof,
to a binding site that induces allosteric modulation in the PCSK9 protein;
whereby the population of said low density lipoprotein receptors is modulated by said conformational shift.

9. The method of claim 8, whereby the population of low density lipoprotein receptors is increased.

10. The method of claim 8, wherein the compound is formulated as a pharmaceutical composition comprising a pharmaceutically acceptable carrier or excipient.

11. The method of claim 8, where the compound is selected from:
- 1-(4-benzylphenyl)piperazine;
- 1-(4-(benzyloxy)phenyl)piperazine;
- 1-(4-phenoxyphenyl)piperazine;
- 1-(4-(4-(methylthio)phenoxy)phenyl)piperazine;
- 4-(4-(piperazin-1-yl)phenoxy)benzoic acid;
- 4-(4-(piperazin-1-yl)phenoxy)benzamide;
- 5-(4-(piperazin-1-yl)phenoxy)picolinamide;
- 1-(4-(3,4-dimethylphenoxy)phenyl)piperazine;
- 4-(4-phenoxyphenyl)piperidine;
- 4-(4-((tetrahydro-2H-pyran-4-yl)oxy)phenyl)piperidine;
- 4-(4-(piperidin-4-yl)phenoxy)piperidine;
- 1-(4-((tetrahydro-2H-pyran-4-yl)oxy)phenyl)piperazine;
- 1-(4-(piperidin-4-yloxy)phenyl)piperazine; and
- 1-(4-phenoxyphenyl)piperazin-2-one;

or a pharmaceutically acceptable salt thereof.

12. A method of inhibiting PCSK9 in a mammal by administering to said mammal a pharmaceutical composition comprising a compound of Formula I:

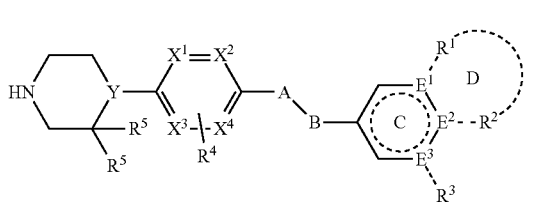

wherein
- A is —O— or —CH$_2$—;
- B is —CH$_2$— or absent;
- Ring C is a 5 or 6 membered heteroaryl or heterocyclic ring, or a 6 membered aryl ring;
- E$^1$, E$^2$, and E$^3$ are independently selected from C, CH, and N, wherein one of E$^1$, E$^2$, and E$^3$ may be absent;
- R$^1$ and R$^2$ are independently selected from the group consisting of H, lower alkyl, hydroxy, amino, aminoalkyl, hydroxyalkyl, haloalkyl, carboxy, —CONH$_2$, —CONH-alkyl, nitrile, —S-alkyl, —O-alkyl, acyl, and oxo; or R$^1$ and R$^2$ with the atoms attached thereto combine to form a 5-6 membered fused aryl, heteroaryl, carbocyclic or heterocyclic ring D containing 0-3 heteroatoms, where Ring D may further be substituted at a position two atoms away from the juncture with Ring C;
- R$^3$ is selected from the group consisting of H, lower alkyl, hydroxy, amino, aminoalkyl, hydroxyalkyl, haloalkyl, carboxy, —CONH$_2$, —CONH-alkyl, nitrile, —S-alkyl, —O-alkyl, acyl, and oxo;
- R$^4$ is selected from the group consisting of H, OH, halogen, and lower alkyl;
- each R$^5$ is hydrogen or both R$^5$ taken together are oxo;
- Y is selected from the group consisting of N and CH; and
- X$^1$, X$^2$, X$^3$, and X$^4$ are independently selected from the group consisting of CH, C—R$^4$, and N; or a pharmaceutically acceptable salt, hydrate, or solvate thereof.

13. The method of claim 12, whereby the LDL levels in said mammal are decreased.

14. The method of claim 12, for treating hypercholesterolemia in a mammal in need thereof.

15. A method of inhibiting PCSK9 in a mammal by administering to said mammal a pharmaceutical composition comprising a compound selected from:
- 1-(4-benzylphenyl)piperazine;
- 1-(4-(benzyloxy)phenyl)piperazine;
- 1-(4-phenoxyphenyl)piperazine;
- 1-(4-(4-(methylthio)phenoxy)phenyl)piperazine;
- 4-(4-(piperazin-1-yl)phenoxy)benzoic acid;
- 4-(4-(piperazin-1-yl)phenoxy)benzamide;
- 5-(4-(piperazin-1-yl)phenoxy)picolinamide;
- 1-(4-(3,4-dimethylphenoxy)phenyl)piperazine;
- 4-(4-phenoxyphenyl)piperidine;
- 4-(4-((tetrahydro-2H-pyran-4-yl)oxy)phenyl)piperidine;
- 4-(4-(piperidin-4-yl)phenoxy)piperidine;
- 1-(4-((tetrahydro-2H-pyran-4-yl)oxy)phenyl)piperazine;
- 1-(4-(piperidin-4-yloxy)phenyl)piperazine; and
- 1-(4-phenoxyphenyl)piperazin-2-one;

or a pharmaceutically acceptable salt thereof.

* * * * *